(12) United States Patent
Yaver et al.

(10) Patent No.: US 6,372,464 B1
(45) Date of Patent: Apr. 16, 2002

(54) POLYPEPTIDES HAVING PEROXIDASE ACTIVITY AND NUCLEIC ACIDS ENCODING SAME

(75) Inventors: Debbie S. Yaver; Barbara McArdle, both of Davis, CA (US)

(73) Assignee: Novozymes Biotech, Inc., Davis, CA (US)

(*) Notice: Subject to any disclaimer, the term of this patent is extended or adjusted under 35 U.S.C. 154(b) by 0 days.

(21) Appl. No.: 09/596,824

(22) Filed: Jun. 19, 2000

(51) Int. Cl.$^7$ .............................. C12N 9/08; C12N 1/20; C12N 15/00; C07K 1/00; C12Q 1/68
(52) U.S. Cl. .................... 435/192; 530/350; 435/320.1; 435/252.3; 435/6
(58) Field of Search .............................. 435/192, 252.3, 435/6, 320.1; 530/350; 536/23.2

(56) References Cited

PUBLICATIONS

GeneSeq Database, Accession No. W12392, May 1997.*
Huang et al., J. Agric. Food Chem. 44:3437, 1996.
Agbola et al., J. Agric. Food Chem. 46:84, 1998.
Mester et al., 1998, *Journal of Biochemistry* 273: 15412–15417.

* cited by examiner

*Primary Examiner*—Rebecca E. Prouty
*Assistant Examiner*—M. Monshipouri
(74) *Attorney, Agent, or Firm*—Robert L. Starnes

(57) ABSTRACT

The present invention relates to isolated polypeptides having peroxidase activity and isolated nucleic acid sequences encoding the polypeptides. The invention also relates to nucleic acid constructs, vectors, and host cells comprising the nucleic acid sequences as well as methods for producing and using the polypeptides.

15 Claims, 12 Drawing Sheets

```
CCATGGTATGTCGTTTGGTTCCGTCGGGACAGTTCGAGTTCGCCGAGAACGGTGCGTCCCGCCTTTGAAT    70
ACTCTGAAATGGCCCCGTTAATGAATGTCCATTCAGATGAAGCGCGAGAGGTGTACCTTGTAGAGCTCAC   140
ATCCAACTGTCCCGACGCACTGGAATTGTCACAAGGCCCTAGACTTTGGGTCCCTAGGACGTCAAAAAAC   210
CGTGTTCGACCTGCGTCTTACAACCTTCCGATGTTTCTGTTGACACGGGCAGGAACGATAACGTGTGTAG   280
AGCTCCAAGTTTAGTTGGCCAACATGCCTCTAAAGACATGGTTTTGGTCCTGCCGTCTCACCCTTACT    350
CATGCCAATACCAGCCTCAAGCCTGAGAGGAATGCCCGCGATGGTATCGCCACGGTGACCCTTTTTGC    420
GCGAGAACATGCCTCGTCAAGGCTGTACCCGATGCGAACTGGGTGCTCAAAGGGGTCCCGACATTCAAC   490
TATTGTGCCAGATGACGAAGGACCAGAAGGGAGGACGGCCATTGGATGGCCGCATGCGAACCGGTG      560
CCGACGGTATGCCAGGTACGCTTTCGGTGCCGCCGTCGTTCTGCTAATGTTTACGATAATAATTCACG   630
GCGGTGTATAAAAGCCACCTCTCCAGTGCAACCTTTCTTCCGCTCTCCGTCGCAATTTCCTAGGCACCGCCCAGG  700
TAGCTGCAATGGCCTTCAAGCAACTCCTCGCTGCCCTCAGTGTGGCGATTACCAGGACGTGT  770
                                                                        840
    M  A  F  K  Q  L  L  A  A  L  S  V  A  I  F  L  G  T  A  Q  G
 M  L  S  T  P                                                R  V
TATGCTCTCTACGCCCGTACTTCCGACCGGCGAACACTGCGAACGCCCATGCTGCCCTTGTTCGCCGTTCGCCGACGAC  910
 A  C  P  D  G  V  N  T  A  T  N  A  A  C  C  A  L  F  A  V  R  D  D
TGCCTGCCCCGACGGGGTGAACACTGCTGAACACTGCGAACGCCGCAATGCTGCCCTTGTTCGCCGTTCGCCGACGAC
 I  Q  A  N  M  F  D  G  G  Q  C  N  D  V  A  H  Q  S  L  R  L
ATCCAGGCCAACATGTTCGACGGCGGCCAGTGCAACGACGTTGCTCACCAGTCCCTGCGCTCTGTGAGTAC   980
                        T  F  H  D  A  V  A  F
AACGGCCAACAGGCCTCACTGACACAAGGCCAGTTCGGGTAAGTTTTCCTCCATACCACCACAAAGGCGTTGGCTGATT  1120
 S  P  A  L  T  A  Q  G  Q  F  G
CTCCCGGCGCTCACTGACACAAGGCCAGTTCGGGTAAGTTTTCCTCCATACCACCACAAAGGCGTTGGCTGATT  1120
```

Fig. 1A

```
AGACTTATCATCAGAGGAAACGGTGCTGATGGTTCTATCATCACCTTCGGTGATATCGAGACGGCCTTCC  1190
          G  N  G  A  D  G  S  I  I  T  F  G  D  I  E  T  A  F
ACCCCAACATCGGCCTGACGAAATCGCCATCCAGAAGCCGTTCATCGCGAAGCACAACATGACAGC      1260
 H  P  N  I  G  L  D  E  I  V  A  I  Q  K  P  F  I  A  K  H  N  M  T  A
TGGCGACTTGTGAGTCTCTTGCAGATAGACTATCATATCTTCAACTCAGTCATTACTTCGGGATTAGCC   1330
 G  D  F
TCCACTTCGCTGGTGCGATTGCTACGACCAACTGCCCTGGTGCTCCCACCATCAGCTTCCTCTTGGGTAA 1400
 L  H  F  A  G  A  I  A  T  T  N  C  P  G  A  P  T  I  S  F  L  L
ATTATATCCACATTATCATCTCATTATTATTGCACCTCAGCCCGTCCCGAGGCTACTC              1470
                                               G  R  P  E  A  T
AGGCTGCTCCTGATGGTCTCGTTCCAGAGCCGTTCCGTGCCTTTCTTTACAGCTGAGCTTCACT        1540
 Q  A  P  D  G  L  V  P  E  P  F
AATGTCGGTACCAAAACCAGACACTGTGACCCAGATTCTGGCCCGCATGAACGACGCACTGGAATTTGAC 1610
  H  T  V  D  Q  I  L  A  R  M  N  D  A  L  E  F  D
GAGCTCGAGACTGTTTGGGCTCTCATTGCCGTGAGTAAAATTTTATCAGTACAATGCTGTTGCTGACTGA 1680
 E  L  E  T  V  W  A  L  I  A
CCTCCAAACCAGCCACACCAGCCTGTGCCCAACGATATGCCAACGATATGACACAACCATCCCGCGACCCCCTTCGAC 1750
                   H  T  G  A  A  N  D  I  D  T  T  I  P  R  T  P  F  D
TCTACGCCGACGCTCTTGACTCCCAGTTCTTCATCGAGACTCAAGGCACCTTGTTCCCGGGT          1820
 S  T  P  T  L  F  D  S  Q  F  F  I  E  T  Q  L  K  G  T  L  F  P  G
AAGCAGAGGCTTGTACATTACACCGGCGGTGACTGACACATGAGCATTAGCACTGGTGGAGACAACGG   1890
                    T  G  G  D  N  G
```

Fig. 1B

```
CGCAAACACAGGGCGAGGTCATGTCCGGTCTCGGCCGTCTGCAGATGCGTCTGCAGTCCGACTTCCTCATCGCC  1960
 A  N  T  G  E  V  M  S  G  L  A  G  E  M  R  L  Q  S  D  F  L  I  A
CGGGACGCGAGGACAGCCTGCAATGGCAATCGTTCTCCGGCAACATGCCCAAGCTCCAGAACCGCTTCC  2030
 R  D  A  R  T  A  C  E  W  Q  S  F  S  G  N  M  P  K  L  Q  N  R  F
AGTTCGTCCTCGAGACCTTTGCTGTCGTCGGCCAGGACCAGACCAACATGATCGACTGCTCCGAGGTCAT  2100
 Q  F  V  L  E  T  F  A  V  V  G  Q  D  Q  T  N  M  I  D  C  S  E  V  I
CCCCGTCCCCGTCGTGGACCTCACCGACGAGCAGGCTGCTGGCTTCTTCCCTCCCGGAAAGACTCTCGATGAT  2170
 P  V  P  V  D  L  T  D  E  Q  A  A  G  F  F  P  P  G  K  T  L  D  D
GTTGAGGGAGCTGTGAGTTCTCTCTTTTTCTCGTGTGCCTACGACTGATTGTACATCGTTCAGTGCG  2240
 V  E  G  A                                                          C
CCGACACTCCGTTCCCCTCGTTCGCTACCGCCCCACTGCTATCCCCGCCGTAAGTTTC  2310
A  D  T  P  F  F  P  S  F  A  T  A  P  G  P  A  T  A  I  P  A  V  .
AAAGCAATTGTGCTCTTGTATTGCGAGCTAATAGCCCCTATAGCCCTCGTCGTCCCCGGTCAACTCACCTAA  2380
GTAGATGTGAGGTTCATCGGATGGAATATCACTCGACAACGGCATGGATATACTGKTTAAGGATYYTWAG  2450
TGGKGTTTTGTATTATATAGTGACCGTGNATGTATGCAG  2489
```

Fig. 1C

```
CAGCGGAATAACCTTAGTCATATACTGAGTAGACGGACGTGTGTATGTGCCTGTAGAGGCTTCTCGGCGCC      70
ATACTTTGAGTTCCGCCCACACGGAGTGACAGAAGGAGACCTGGTCCTGGACCAAAGCAAGACCGCTGTT     140
GTCTGGATCGGAATTCGACAGGACTCAATTTTGAAACAGAAGTTTCGGAGCATAGTTGGTGAAAGTATGA     210
GTCTCGTATATTCCTGGATGGAATTACAGGCCCTTCTCGCGGTAATGCTTGCTTACTCTTATGAGAATA     280
AATGGTGGCGTTCGGAAAAATGCCGCTACCTGTTACTTACCGTCTCTCCCAACCAAATCGACTCGGACTAGAGACCAACGGG     350
GTCAAAAGTGGACTCTCGCGTCTTTCCGTCTCTCCGTCTTCAGGTCAGATGTGCAGACTGTGTTCAAGGTCACTCCGTCCCAACT     420
CGTACGACAACATACATCGATCTTCACATGGACATGTTGCAGACTGTGCATCGTGCGAGAGAACAAGTACTTATAATAGACTTAG     490
CCCGGTAGGCTCGAACCGGTGATACTTACCTCGATCGTGCGAGAGAACAAGTACTTATAATAGACTTAG     560
GGTCGTCGCGGCCAGTACGATGATGGTCGGCATCTCAGTCTCTCGAGGGTGCTATAGTTATGTCTGACG     630
GTACCTGCCCTGACATGGCACTTCGCGCGAAACTTGCGTCGTGAGGTCATGGCCGCCTCGGCTCGTTTG     700
ACAACTGTGTACGCAAAGTGAGTACTCGGGAGCCGTCTGGCTTCACCAGCTCTCCTGCCGCATTACT      770
AAGTCTCCGAAGCGCGCCGATAGTAGCTTGTGTTTTGGATGAGAAACGCTCGGGCAAAACGGCGACTAGC     840
GACATCGTATCGACGACGGCCGGCCGGTCGTCGCGTTACTTGTGTCCGAGACCTCTTCTCACG     910
AGACGGGAGTTATTTTTGTTTCTGAGAATGAACGTTCTCACTTTCCTTTGCAGGATTGCTCAGTCAGTGATGGC     980
ACGCGTTGCCTAGTCAGCCCAACTCGGAGAAGTAGAACCCTAACATGCACTCTGTGTTCAAAGAACACTGCTGCAAGACTACT    1050
CGGGGCAGCAGCCCAACTCGGAGAAGTAGAACCCTAACATGCACTCTGTTCAAAGAACACTGCTGCAAGACTACT    1120
TACCCAGCCGCCACGAAGCCGTTGAAAAGCCTAACATGTCTGTTTCCACAAACGAGTGTACCTCAAACATGGT    1190
GCGGCAGAACGAGACCCTCGGTTCTGCATAAGCCTCTGACATGACGGAGACCGTGTACCTTCAAACATGGT    1260
CCTGGCGCCATTCATAGCGGTAAGATATTTTGATTCTCGCCAGCCCTGACTACTATCAACGAGACCGTGCCACCA    1330
CCAGAAACCGGGCATGCGGCAGTACAGGTCCCCGCCTAAACCTGTACCAATGTTTGGTTCATTC    1400
GACTGCGGCTCATCATACGTCTATGTGCCTGCGTCCCAGCTCCATCAACGTCCCGCGCGAAGCAGGACTATGAGCTTTTGT    1470
ACGGCACCGACAGCCCTCTGTTGATTTGCCGTAAGGCAGCAGTGGACGGCTCGCGCGTGGGAGTCG    1540
GCAGAAGAGACACAGCCCTCTGTTGATTTGCCGTAAGGCAGCAGTGGACGGCTCGCGCGTGGGAGTCG    1610
```

Fig. 2A

```
CCGAGGTTATTTCGGCTCGTGGTACGGGAAAGTTCTGTCTACGGCTGTCGAGACATGGAAATCCGTACC  1680
ACTGGACTGCCAGGCTGGAGAGGGCCGTGGAACCGTGCCCTCAAACGAGGATATTCTCATT          1750
GGCCGCAGCAAAGGAACATCTTGAGAGACAATGTGGCGCTGCAAGCTAGAGGCATACTTCTGCGAAGTA  1820
TAAAGCTGCTAGAGTAGTTGGGACCATCCGTCTTCTACCCTCTACTCAGTCAAACCAG             1890
CAATGGCCTTCAAGCAGCTCGCCACTGTCTCTGCCCTGTCTCCCGCTGTCGAAGTTTGTG           1960
    M   A   F   K   Q   L   L   A   T   V   S   L   A   F   S   L   T   A   V   E
GCGAATTACTCTGCCAGCCACTTGTGCTCTATCGCGTTTAGCCGCCCTTACCGCCGGGTTGCTTG       2030
    A   A   L   T   R   R   V   A   C
CCCCGATGGCGTGAACACCGCGAACGCGGCCTGCTGCTCTCTGTTCGCCATCCGTGACGATCTTCAA    2100
    P   D   G   V   N   T   A   N   A   A   C   C   S   L   F   A   I   R   D   D   L   Q
CAAAGCCTGTTCGACAACGGCGGGATGTGGCGAAGATGTTCACGAGTCTCTCCGTCTGTGAGTATACGACC 2170
    Q   S   L   F   D   N   G   G   C   G   E   D   V   H   E   S   L   R   L
AGCCCCGAATCCCGACCCAAAATCGGGAAAGTTCGGGTGCGTATACATCCAAAATATGATGTCCTCGACT  2240
                          T   F   H   D   A   I   G   I   S   P
CGCCATCGCGGCAACCGGGAAGTTCGGCGACGGCTCTATTGCCATCTTCGAGGACATCGAGACTTCCACGC 2310
    A   I   A   A   T   G   K   F   G
AGTCGCGGCAGAGGTGGAGGTGCCAGCAGGCCCATCAACGAGCAGAGGCCCATCCTGGCCAGACACCACCGCT 2380
        G   G   G   A   D   G   S   I   A   I   F   E   D   I   E   T   N   F   H   A
GAACTTGGGCGTCGACGAGATCATCAACGAGCAGAGGCCCATCCTGGCCAGACACCACCGCT         2450
    N   L   G   V   D   E   I   I   N   E   Q   R   P   I   L   A   R   H   N   I   T   T   A
GACTTGTTCGTCGCTTCCTGATCATTCTCCACTATACTGCTAACCGATCGTTTAGCATTCAGTTTGCTGG 2520
    D   F                                   I   Q   F   A   G
```

Fig. 2B

```
TGCAGTGGGCGTGAGCAACTGCCCCGGTGCCCCTCAGCTCGAGTTCCTCTTCGGTAAGCGAAACCGTCTT  2590
 A  V  G  V  S  N  C  P  G  A  P  Q  L  E  F  L  F

TCATCATAACACATCTACTCAGGCCGACTGTACAGGCCGCACGCGACCCCGACCTCA  2660
                           G  G  R  T  D  A  T  Q  P  A  P  D  L

CCGTCCCGAGCCTTCCGATACCGTCGACTCGTCCATCATCGCTTCGCTGTGAGCTTCACCCC  2730
 T  V  P  E  P  S  D  T  V  D  S  I  I  A  R  F  A  D  A  G  G  F  T  P

CGCGGAGATCGTTGCCCTTCTCGCCTAAGGTTATTTCATACTGCAAAAAGCATCCCGCTGATACACG  2800
 A  E  I  V  A  L  L  A  S

CCACCTATGCAGCAGCCACACCGTTGCCGGCGACCCACCATTCCGGAACTCCATTCGAC  2870
       H  T  V  A  A  A  D  H  V  D  P  T  I  P  G  T  P  F  D

TCGACCGCCTCTACCTTCGACTCCCAGTTCTTCGTCGAGACGCTCTTCAAGGCTCTTCCCGGTAC  2940
 S  T  A  S  T  F  D  S  Q  F  F  V  E  T  L  L  K  G  T  L  F  P

GCCTACCTTCGATCCGACTTCCCCTTGCATTCTGACATTAGCAACAGAACTTCGGGCAACGTCGGA  3010
                 F  F  V  E  T  L  L  K  G  T  L  F  P

GAGGTGATGTCCCCCATCGCGGGGGTGAGAATGCGGCTCCAGTCCGAGCTCGCACAAGACTCTCGTA  3080
 E  V  M  S  P  I  A  G  E  M  R  L  Q  S  D  F  E  L  A  Q  D  S  R

CTGCTTGCGAGTGGCAGTTCGTCAAGGAGACAATCAAGATCGCCCGCCGGATTCTCTG  3150
 T  A  C  E  W  Q  S  F  V

ACCGTACACCAGAGCCAGATGGTCGACTGCTCCGAGGTGCTGCCGAGGGTCTCCAGGTCTGACCGCCACTCTCCG  3220
 N  N  Q  D  K  I  K  T  A  F  A  A  F  A  K  M  A  T  L

CGGAAATGACAGAGCCAGATGGTCGACTGCTCCGAGGTGCTGCCGAGGGTCTCCAGGTCTGACCGCCACTCTCCG  3290
 G  N  D  R  S  Q  M  V  D  C  S  E  V  L  P  R  V  S  T  A  T  L  P
```

Fig. 2C

```
CCCGGCCACCTCCCCGCCAAGACTCGCGGCAGCAGGCTGTACGCACTTCATATTCACTCT  3360
 P  A  H  L  P  A  G  K  T  L  A  D  V  Q  Q  A
GTGCGCGAGAAGTTGAGCTGACGATACCTGCTTCAGTGCGCCACCCCCTTCCCGTCTCTGCCG  3430
                                C  A  D  T  P  F  P  S  L  S  A
ACCCCGGCCCGGCCACCACTGTCCCCCCTGTGTAAGTGTTATACGATACAATCCCTCAGCCGACGGTGTG  3500
 D  P  G  P  A  T  T  V  P  P  V
CTAACGTGATAAATTCGTGTGCAGCCCGCCTTCCTAAGTTGCCATCTCTAGTCAGTCGAGACGGTATATCGACT  3570
GAGGCGTCGTCTCATCTGTCGGAAGTAGAAGTTCTGCGAATGTATCTATCTGTTGATTCGAATGGGGATC  3640
CGCTTTGTGAAC  3653
```

Fig. 2D

```
CGCATCTTCATCCCCGGCACGAAGGGCCTGCAGCTTGCCCGCGGTAAATTTCGCGCGCCATACGGTCCAAA      70
GTATCTATAACATCCTTCAATTCGTGTGTATGGCCCGCGTTGGCGCCGTGCTCCACGAGGAATCGCTTACCC     140
GCGATGATGGATATACTTCACGAGTGGAGAGAAGCAAAGACAGCGCATTTGCGAGGGCCGGCCT             210
GGAAAGCGCTAGATGTGAGTTCCGAGATCCACTCTTTCTGCCGATGCTCACACTATGTGCTTGACTG          280
CTTCCGCATACTCGTTGCGAGTGTCTTCGACAAGGCTGTCAACAAGCTGTCCATAGAGTAGCCCATACCGCCTGTCCAAT      350
AAGCTCCAATGCACGCCCAATCATCTAAGCCATCTAAGCCATTCGACAGTCCAATTCGACACACTTTCTGATCCCTGACCTG   420
CCGGCGATGCCATCCTTGAGCTGAGTCAAGTTGATTAATATATGCCGGTACCGGCAAGACA               490
CCTACGCGGTGGACGTCTCGTAGAACACAGGCGTTAGGTTCTTCATATTCCCAGCGATGTCAAGCGGCCG      560
TGAGCAGCTTCCTTGGCGCGTGGTGATGACCTAGAACGGTCCGACGCATGTCAAGGTGAACGGCCG          630
ATGCAGACTCGTAGGACACTGCTTACCAGTGGATAACAGCCCAGGCCGAAGACAATGTTTCGATAT          700
CTGAAGGATGTGCACACGGTTCAGTGCACGGTTCGAGATGGAGAACGGAATTGGATAACTCACGCGAG        770
TACGTAGTTTGGTTCCGGATACATGTCGAAAAACAAACTGACCACTGCACGCCTTCGGGTCAAAC           840
ACGTAAAGCCCCCTCGCTGAAACGGAACTGACCACTGCACGCCTAGAGAGGATCACGCA                 910
CGCCCGAACAACGAAGAGCTGTTTGAAGTTTCCTGAGAGGAGTCAAAGTCTAGCGCCGAGATTGTAC         980
GCCTTCTCGCTGACCTTACCCTGTGTGAGGAATGAAGGGGAGGCCCACAACAAAGGAAATGCCCGCCGATGGTGCGAG 1050
GACTCTCGACCTTCAATGTGGCTCTTGCTCACCAAGTATCTTGTCTAGAGCGATTCCAC                 1120
GGTCAACGCACGAAGACCTTCCATATCAGCCATGCCACAACAAAGGAAATGCCCGCCGATGGTGCGAG        1190
AGCCGTCATGGTCGTAGTAGAAGTGCGCAGACGTGGGGATGGCGAGTCGTCTGTTTCGCCTTGATGTCCGACC   1260
GTAGCCGTCGGGTGAGCGTTAGCGAAGCAGCCGTCATCACTGTCGTTAGTAACACAAGAT                1330
CTCCGCGGTTTCAATGTGGCTCTTGCTCTTGCTCCCACACCAAGTGAGCTTCAACCCGCGAGGGGTGTTCAACCGCAGTA 1400
GCTTCGGAAACCCCTCCTCCCACACCAAGTGAGCTTCAACATGAATTAATCGTCAAGCACTACCCGCAG       1470
CTGTTGAAGTACAAAGGTAGTGATAATCAGGAAAAACCTGAGTGTGAGAGATAAAAGACTATTTCCTGCAGCGA  1540
CCGACGGCCGGATATCGTCTTCAGGCTGTTGTTTGATTGTTAAAAAGACTATTTCCTGCAGCGAAAC         1610
```

Fig. 3A

```
TTTATAGAACCCATCGTTGCTGCGGTCATGATCGAAGTTAACAGGTGCCTGTCAAAGTCAGGCCCATT      1680
TGTAGCATTTGTTGGACATAGTGGGCACCAACCTTGGCGTTGAAGACAAGAGAACGAATGACGATTCGGG   1750
AATTGGATCAGCATGCTGGACGTCTCCGCCAGTATTATCTACACTCGTATTCTTCCTCCGAA           1820
TGTTGCGGAGCGGACTAGGAACAGGACCGCGGAGAACAGGACCGCGGTACACTCGTATTCTTCCTCCGCA   1890
GCGAGTGTTTGAACAGGACTGTCGCTTCGATTTGTTTCTGTACCAGATACTTCTATCCGATTGCGCGG    1960
CGTCGGATGTGCTCGCGGATGTGCTGACCTTCATCCAGCCCCTCTGTGCCCCTGGTTTTACAGGTTATTTTTGAAGCCCG   2030
AACTTCCATCTCCTGCTTCTCCTGCTTCTCTACGGACTGCCCCGTACAAATGTGAAGAGCGACATCGCGCTCCGCAGGCCT   2100
CTGTGACCTCCAGGAATTCTCTACAGCGGGACCCTGCAGGTACGTGGGTCGGTGCTGGCGCCACCCAGAC   2170
TCGGCTTGCCAACGATTGCCTTTTCTATAGACCGAGTGTGGGTCGGTGCTGGCGCCACCCAGAC         2240
CTCCTCCGGAATGTAGTTCGTGCTGTGTGCAGTAGTTGCACCACTGGAAACATGCACTGCTTGCACAGGGC 2310
GCCAAATGCGGTCGCCTCTCGCGGTACCTATTGCACTGCTTGCAGGGCTTCTCGCGTATCAAGCC       2380
ACTGGCGAATACATCACAAGCGGGCCCGTGCGTGAGCTGCGTTGCACAGCAGTCTGTAGAGTCCAGCT    2450
CTCGAATACAAACAGACTGGTCGGGCAGGCCGGTCGCGCGGCCCGTGCGTGAGCTGCGTTGCACAGCAGTCTGTAGAGTCCAGCT 2520
CAGCGACGACCACGGTCCGCGCGACGAGGTTGGCGCTGTTGGCTTGCGGCTGATTCAGCCGATCCTAT   2590
TGGGCCCGGCGGCTGTTGGCGATCACAGATCACCACCATACCACTTCCAGTATAAAGAGCGCCGGGTATGCAAGCG  2660
CGTCGCGCTGGCGGATCACAGATCACCACCATACCACTTCCAGTATAAAGAGCGCCGGGTATGCAAGCG   2730
AACACCTCATCGTGCCCCTTCCCTTCTCCTTGTTGTCTGTTGCTATCCAGCCGCAGCCGGTACGCCACATAATGG  2800
                                                        M V           2870

TCTACAGACTCTCCTCCCTGTTGTCTGTTGCTATCCAGCCGCAGCCGGTACGCCACATAATGG          2870
 F Y R L S  L L V S V A A I H A A A
CTCCCCCCTCCCGATCCACGCTGACCAGCTTGCTAGGTGCTCTGACGCCGTGTGCCATGCCCGATGG     2940
 G A L T R R R V A C P D G
```

Fig. 3B

```
CGTGAACACCGGCGACCAACGCGGCGGTGCTGCCCCTTGTACGCGCGTCCGGCGATGACATGCAGGCCAACCTG   3010
 V  N  T  A  T  N  A  A  C  C  P  L  Y  A  V  R  D  D  M  Q  A  N  L
TATGATGGTGGCCGTGCAACGCCGAGGTGCATGAGTCCCTCCGCCTTGTAGTACCCAGCTTGCTTTCGG        3080
 Y  D  G  G  A  C  N  A  E  V  H  E  S  L  R  L
TGTTGCACAAAGCTCATCTAGTGCCAGCACGACGCCATTGTACGTCTTGCTTAGATTTCTTC               3150
                                 T  F  H  D  A  I
CAACGGGTGTCTTACGATATTCTACAGGCCCTCGCGCCGGCTCATTCGCAGGTGGA                     3220
                 G  Y  S  P  A  L  A  A  A  G  S  F  A  G  G
GGAGCTGACGGCTCTATCCTTACCTTCAGCGATGTTGAAGCGGCCTTCTTTGCCAACGGGTCTCGACG         3290
 G  A  D  G  S  I  L  T  F  S  D  V  E  A  A  F  F  A  N  A  G  L  D
AGATGATCGAGCTCCAGAAGCCATACATCACCAAGTACAACATGACTCCTGGCGATGTGTACGTACCAGG      3360
 E  M  I  E  L  Q  K  P  Y  I  T  K  Y  N  M  T  P  G  D  V
AACCCTCTTTGGCGATATTATACTGAAGCGTTCTCTATAGCGTTCAATTTGCTGGCCCGTCGGTCTCAGTA     3430
                                                V  Q  F  A  G  A  V  G  L  S
ACTGCCCAGGTGCTCCGCAACTGGAGTTCCTTCTGGTACGGCCAATAAATCAGACGCGAAAGCCA           3500
                 Q  L  E  F  L  L
CGTTCTGATCATGCCCAGGTCGTACTGCCGCGTTCGCGCTTCGACTTCAGCGTTGACGAGATTGTAGCGCT    3570
 G  R  T  A  A  T  A  A  S  P  T  G  L  I  P  A  P
TTGACACGGTCGATGCAGATCATTGCCCGCTTCGCCGTTGACGACTTCAGCGTTGACGAGATTGTAGCGCT    3640
 F  D  T  V  D  A  I  A  R  F  A  D  V  D  F  S  V  D  E  I  V  A  L
GTTGGCATCGTAAGCACGCCCCCTTTGCTTGGCCGAGCATCATGATTAACGACGTCTCACTTGCAGGCACT    3710
 L  A  S                                                              H
```

Fig. 3C

```
CGGTCGCCGCTGCAAGCCACATGACACCACCGTTCCTGAGTCGCCGCTCGACTCGACCCCTGGCGTCTT   3780
 S  V  A  A  A  S  H  I  D  T  T  V  P  E  S  P  L  D  S  T  P  G  V  F
CGACACCCAGTTCTTCGTCGAAACCTCGCTCAACGGCACCATGTACCCTGGTACCTCTGGAAACATCGGC   3850
 D  T  Q  F  F  V  E  T  S  L  N  G  T  M  Y  P  G  T  S  G  N  I  G
GAGGCCCTGTCAGCGATTGCGGGAGAGCTTCGCCTGCTCTCGGACCATGAGCTCGCGCGTGACTCGCGCA   3920
 E  A  L  S  A  I  A  G  E  L  R  L  L  S  D  H  E  L  A  R  D  S  R
CTGCCTGCGAGTGGCAGTCCTACGTCAGTACGTACCCTGTCCTTCGGTTCCGTTGACGGTTTCCATTTAT   3990
 T  A  C  E  W  Q  S  Y  V
GCTTTACGTGTGCAGACAACCAGTCCTGACCATGATTGACTGCACCGAAGTCATCCCACCGTCCTTCACCTCC   4060
         N  N  Q  S  K  I  Q  S  A  F  R  A  A  M  A  R  M  A  V
CATCGGCCAGGACTCCTGACCATGATTGACTGCACCGAAGTCATCCCCACCGTCGTCCTTCACCTCC   4130
 I  G  Q  D  S  T  M  I  D  C  T  E  V  I  P  T  A  S  S  F  T  S
GCCGGCGTTTATCCCGCCGGTCTCCACGCTACGGTGCCGACTGTGCCGACTCCACTCCCTTCCCCA   4200
 A  A  F  I  P  A  G  L  T  Y  A  D  I  E  Q  S  C  D  S  T  P  F  P
CCCTTTCTGTCGTTGCGGCCGCCAGGTCCGTTGCGGTGTTTCGGTTCCTCTCAA   4270
 T  L  S  V  V  A  G  A  A  T  S  V  A  A  V  A  .
ATTCCACATAGTACTGACAAATATTTAGAAAAATCATAAACTGCCCACACCGGCAACCCCTGGCTTCTAT   4340
TCTATCTTTTGGGTTAATATGGACTTCTTGAACACTGTGGTTGAAATTAGTACTGTCG   4410
CTACCTGCCCGACCTTGTAAACACTGTCTCTACGAGTAAATAGCCCGCTCCAAAACCGTCTATC   4480
TATAGAGGTATCCACTGCCAAATGTCATCGCTATTATCGTCTACATTTGCTGCGACATAAAAACCC   4550
GATATGGACTTCTCGTCGTTGCCGCGCAGCAAAGCGGTCTAACGGTCTAACCGCAAATGCAGGTATGTTTT   4620
```

Fig. 3D

```
GAAATCTCGGCCTGCTGTTGTACCTCAAAATACTCAAGTACGTTCTCACATGTTCGCGATGACCGTAC  4690
AGCAACTCCACGGTTGTGGCGAAGCAGTCGAAAATTAAATGGAGCAGCACCACTCACTTGGCATCTGCC  4760
ATGTCACGGGTCCCTCTGAGTCTGAGCCAAGACAAAACTGGATCGGGGCAT  4810
```

Fig. 3E

SEQUENCE LISTING

<160> NUMBER OF SEQ ID NOS: 10

<210> SEQ ID NO 1
<211> LENGTH: 2489
<212> TYPE: DNA
<213> ORGANISM: Bjerkandera adusta
<220> FEATURE:
<221> NAME/KEY: misc_feature
<222> LOCATION: (0)...(0)
<223> OTHER INFORMATION: n= A, C, G orT
<221> NAME/KEY: misc_feature
<222> LOCATION: (0)...(0)
<223> OTHER INFORMATION: k= G or T
<221> NAME/KEY: misc_feature
<222> LOCATION: (0)...(0)
<223> OTHER INFORMATION: y= C or T
<221> NAME/KEY: misc_feature
<222> LOCATION: (0)...(0)
<223> OTHER INFORMATION: w= A or T

<400> SEQUENCE: 1

```
ccatggtatg tcgtttggtt ccgtcgggac agttcgagtt cgccgagaac ggtgcgtccc      60
gcctttgaat actctgaatg gccccgttaa tgaatgtcca ttcagatgaa gcgcgagagg     120
tggtaccttg tagagctcac atccaactgt cccgacgcac tggaattgtc acaaggcsct     180
agactttggg tccctaggac gtcaaaaaac cgtgttcgac ctgcgtctta caaccttccg     240
atgtttctgt tgacaccggc aggaacgata acgtgtgtag agctccaagt ttagttggcc     300
caacgcctcc ttaaagacat ggttttgggt cctgccgtct caccttact catgccaatg      360
ccaataccag cctggagagg gaatgccgc gatggtatcg cccacggtga ccctttttgc      420
gcgagaacat gcctccgtca aggctgtacc cgatgcgaac tgggtgctca aagggtccc      480
gacattcaac tattgtgcca gatgacgaag gaccagacaa aggggaggac ggccattgga     540
tggccgcatg cgaaccggtg ccgacggtat gccaggtatg ctttcggtgc cgccgcgtcg     600
ttctgctaat gtttacgata ataattcacg gcggtgtata aaagccacct ctccagtgca     660
accttttcttc caagacacag tcttcctctc aacagtcttc tagctgcaat ggccttcaag     720
caactcctcg ctgcgctctc cgtcgcaatt ttcctaggca ccgcccaggg tatgctctct     780
acgccgtacc tccgaccgcc accgtcctga ctgcttttca ggtgcgatta ccagacgtgt     840
tgcctgcccc gacggggtga acactgcgac gaacgccgca tgctgcgcct tgttcgccgt     900
tcgcgacgac atccaggcca acatgttcga cggcggccag tgcaacgacg ttgctcacca     960
gtcgctccgt ctgtgagtac aacggccaac aggctgcatt cgccatactc acccatcgac    1020
tcaggacttt ccacgatgca gtcgcgttct ctcccgcgct cactgcacaa ggccagttcg    1080
ggtaagtttt cctccatacc acacaaagcg ttggctgatt agacttatca tcagaggaaa    1140
cggtgctgat ggttctatca tcaccttcgg tgatatcgag acgccttcc accccaacat     1200
cggcctcgac gaaatcgtcg ccatccagaa gccgttcatc gcgaagcaca acatgacagc    1260
tggcgacttg tgagtctctt gcagatagac tatcatatct tcaactcagt cattacttcg    1320
gcgattagcc tccacttcgc tggtgcgatt gctacgacca actgccctgg tgctcccacc    1380
atcagcttcc tcttgggtaa attatatcca cattatcatc tcattattat ccaactaatt    1440
attgcacctc aggccgtccc gaggctactc aggctgctcc tgatggtctc gttccagagc    1500
cgttccgtgc gtgtgccttt ctttacagct gagcttcact aatgtcggta ccaaaaccag    1560
acactgtcga ccagattctg gcccgcatga acgacgcact ggaatttgac gagctcgaga    1620
```

-continued

```
ctgtttgggc tctcattgcg tgagtaaaat ttttatcagt acaatgctgt tgctgactga  1680
cctccaaacc agccacacca ctggtgccgc caacgatatc gacacaacca tcccgcgcac  1740
ccccttcgac tctacgccga cgctcttcga ctcccagttc ttcatcgaga cccagctcaa  1800
gggcaccttg ttccccgggt aagcagaggc ttgtacatta caccgcgcgt agtggactga  1860
cacatgcatt agcactggtg gagacaacgg cgcaaacaca ggcgaggtca tgtccggtct  1920
ggccggcgag atgcgtctgc agtccgactt cctcatcgcc cgcgacgcga ggacagcctg  1980
cgaatggcaa tcgttctccg gcaacatgcc caagctccag aaccgcttcc agttcgtcct  2040
cgagaccttt gctgtcgtcg gccaggacca gaccaacatg atcgactgct ccgaggtcat  2100
ccccgtcccc gtcgacctca ccgacgagca ggctgctggc ttcttccctc ccggaaagac  2160
tctcgatgat gttgagggag ctgtgagttc tcttttctt ttctcgtgtg cctacgactg  2220
attgtacatc gttcagtgcg ccgacactcc gttcccctcg ttcgctaccg cccctggccc  2280
cgccactgct atccccgccg tgtaagtttc aaagcaattg tgctcttgta ttgcgagcta  2340
atagccccta tagcccgtcg tccccggtca actcacctaa gtagatgtga ggttcatcgg  2400
atggaatatc actcgacaac ggcatggata tactgkttaa ggatyytwag tggkgttttg  2460
tattatatag tgaccgtgna tgtatgcag                                    2489
```

<210> SEQ ID NO 2
<211> LENGTH: 389
<212> TYPE: PRT
<213> ORGANISM: Bjerkandera adusta

<400> SEQUENCE: 2

```
Met Ala Phe Lys Gln Leu Leu Ala Ala Leu Ser Val Ala Ile Phe Leu
 1               5                  10                  15

Gly Thr Ala Gln Gly Met Leu Ser Thr Pro Arg Val Ala Cys Pro Asp
                20                  25                  30

Gly Val Asn Thr Ala Thr Asn Ala Ala Cys Cys Ala Leu Phe Ala Val
            35                  40                  45

Arg Asp Asp Ile Gln Ala Asn Met Phe Asp Gly Gly Gln Cys Asn Asp
        50                  55                  60

Val Ala His Gln Ser Leu Arg Leu Thr Phe His Asp Ala Val Ala Phe
 65                  70                  75                  80

Ser Pro Ala Leu Thr Ala Gln Gly Gln Phe Gly Gly Asn Gly Ala Asp
                85                  90                  95

Gly Ser Ile Ile Thr Phe Gly Asp Ile Glu Thr Ala Phe His Pro Asn
            100                 105                 110

Ile Gly Leu Asp Glu Ile Val Ala Ile Gln Lys Pro Phe Ile Ala Lys
        115                 120                 125

His Asn Met Thr Ala Gly Asp Phe Leu His Phe Ala Gly Ala Ile Ala
    130                 135                 140

Thr Thr Asn Cys Pro Gly Ala Pro Thr Ile Ser Phe Leu Leu Gly Arg
145                 150                 155                 160

Pro Glu Ala Thr Gln Ala Ala Pro Asp Gly Leu Val Pro Glu Pro Phe
                165                 170                 175

Ala Ala Thr Gly Thr Cys Gly Gly Thr Ala Cys Cys Ala Ala Ala Ala
            180                 185                 190

Cys Cys Ala His Thr Val Asp Gln Ile Leu Ala Arg Met Asn Asp Ala
        195                 200                 205

Leu Glu Phe Asp Glu Leu Glu Thr Val Trp Ala Leu Ile Ala His Thr
    210                 215                 220
```

```
Thr Gly Ala Ala Asn Asp Ile Asp Thr Thr Ile Pro Arg Thr Pro Phe
225                 230                 235                 240

Asp Ser Thr Pro Thr Leu Phe Asp Ser Gln Phe Phe Ile Glu Thr Gln
            245                 250                 255

Leu Lys Gly Thr Leu Phe Pro Gly Thr Gly Asp Asn Gly Ala Asn
        260                 265                 270

Thr Gly Glu Val Met Ser Gly Leu Ala Gly Glu Met Arg Leu Gln Ser
        275                 280                 285

Asp Phe Leu Ile Ala Arg Asp Ala Arg Thr Ala Cys Glu Trp Gln Ser
    290                 295                 300

Phe Ser Gly Asn Met Pro Lys Leu Gln Asn Arg Phe Gln Phe Val Leu
305                 310                 315                 320

Glu Thr Phe Ala Val Val Gly Gln Asp Gln Thr Asn Met Ile Asp Cys
                325                 330                 335

Ser Glu Val Ile Pro Val Pro Val Asp Leu Thr Asp Glu Gln Ala Ala
            340                 345                 350

Gly Phe Phe Pro Pro Gly Lys Thr Leu Asp Asp Val Glu Gly Ala Cys
        355                 360                 365

Ala Asp Thr Pro Phe Pro Ser Phe Ala Thr Ala Pro Gly Pro Ala Thr
    370                 375                 380

Ala Ile Pro Ala Val
385
```

<210> SEQ ID NO 3
<211> LENGTH: 3653
<212> TYPE: DNA
<213> ORGANISM: Bjerkandera adusta

<400> SEQUENCE: 3

```
cagcggaata accttagtca tactgagtac acggacgtgt gtatgtgcct gtagaggctt      60
ctcggcggcc atactttgag ttccgcccac acggagtgac agaaggagac ctggtcctgg     120
accaaagcaa gaccgctgtt gtctggatcg gaattcgaca ggactcaatt ttgaaacaga     180
agtttcggag catagttggt gaaagtatga gtctcgtata ttcctggatg gaattacagg     240
cccttttctcg cggtaatgct tgcttactct tatgagaata aatggtggcg ttcggaaaat     300
gccgctacct gttacttacc gtgggatttt gttgcacctt actatcacac gtcaaaagtg     360
gactcttgcg tctttccgtc tctctcccaa ccaaatcgac tcggactaga gaccaacggg     420
cgtacgacaa catacatcga tcttcacatg gacaatgttg cagactgttc aaggtcactc     480
cgtcccaact cccgggtagg ctcgaaccgg tgatacttac ctcgatcgtg cgagagaaca     540
agtacttata atagacttag ggtcgtcgcc ggcaggtacg atgatggtcg gcatctcagt     600
ctctcgaggg tgctatagtt atgtctgacg gtacctggcc ctgacatggc acttcgcgcg     660
aaacttgcgt cgtgaggtca tggccgcctc ggctcgtttg acaactgtgt acgcaaaggt     720
gagtactcgg ggagccgtct ggcttcacca gctactcctg ccgcattact aagtctccga     780
agcgcgccga tatgtagctt gtgttttgga tgagaacgct cgggcaaaac ggcgactagc     840
gacatcgtat cgacgaccgg cggccgcggt ctctaaaggc catatggaca taatcctcga     900
atgatcgaaa agacgggagt tattttttgtt ttctgtgcgt catacgacgg tttacttgtt     960
gtccgagacc tcttctcacg acgcgttgcc tagtcgagaa tgaacgttct cactttcctt    1020
ttgcaggatt tggctcagat cagtgatggc gcggcagcc caactcggag aagtaggaat    1080
ttgcacttct gtgttcaaag aacactgctg caagactact tacccagccg ccacgaagcc    1140
```

-continued

```
gttgaaaagc ctaaccatag tctgttttcc atgtctaggc atcgcaagag gcggcagaac    1200
gagacctcgt cttcggttct gacatgacgg accgacaaac gagtgtacct caaacatggt    1260
cctggcgcca ttcatagcgg taagatattt gattctcgcg ttaaacctgt accaatgttt    1320
tggttcattc ccagaaaccg tgcgatgcgg cagtacagg tcccagcctt cgcgtgaagc     1380
gagtactacg cagcaccacc gactgcggct catcatacgt ctatgtggcc tgccgactac    1440
tatcaacgac cgcggatgcg tgcccacgca acggcaccga cggcgctgct gtccagctcc    1500
atcaacggtc ccgcgcgaag caggactatg agcttttgt gcagaagaga cacagccctc     1560
tgttgatttt gccgtaaggc agcagtggac ggctcgcgcg tggggagtcg ccgaggttat    1620
tttcggctcg tggtacggga aagttctgtc tacggctgtc gagacatgga aatccgtacc    1680
actggactgc gaggctggag gcgaaccgtg gaagagggcc ggagtgccct caaacgagga    1740
tattctcatt ggccgcagca aagggaacat cttgagagac aatgtggcgc tgcaagctag    1800
aggcatactt ctgcgaagta taaaagctgc tagagtagtt gggaccatcc tcaggacatc    1860
cgtcttctac cctctactca gtcaaaccag caatggcctt caagcagctc ctcgccactg    1920
tctctctcgc cttctccctc accgctgtcg aaggtttgtg gcgaattact ctgccagcca    1980
cttgtgctca tctatcgcgc tttagccgcc cttacccgcc gggttgcttg ccccgatggc    2040
gtgaacaccg cgacgaacgc ggcctgctgc tctctgttcg ccatccgtga cgatcttcaa    2100
caaagcctgt tcgacaacgg cggatgtggc gaagatgttc acgagtctct ccgtctgtga    2160
gtatacgacc agccccgaat cccgacccaa aatctaaccg gatatactag caccttccac    2220
gacgctatcg gtatttctcc cgccatcgcg gcaaccggaa agttcgggtg cgtatacatc    2280
caaaatatga tgtctcctcg cgttctgact agtcgcgcag aggtggaggt gccgacggct    2340
ctattgccat cttcgaggac atcgagacca acttccacgc gaacttgggc gtcgacgaga    2400
tcatcaacga gcagaggccc atcctggcca gacacaacat caccaccgct gacttgttcg    2460
tcgcttcctg atcattctcc actatactgc taaccgatcg tttagcattc agtttgctgg    2520
tgcagtcggc gtgagcaact gccccggtgc ccctcagctc gagttcctct tcggtaagcg    2580
aaaccgtctt tcatcataac acatctactc acgcgactgt acaggccgca cggacgccac    2640
ccagcccgcc cccgacctca ccgtccccga gccttccgat accgtcgact ccatcatcgc    2700
tcgcttcgct gacgctggag gcttcacccc cgcggagatc gttgcccttc tcgcctcgta    2760
aggttatttc atactgcaaa aagcatcccg ctgatacacg ccacctatgc agccacaccg    2820
ttgccgcggc cgaccacgtc gaccccacca ttccgggaac tccattcgac tcgaccgcct    2880
ctaccttcga ctcccagttc ttcgtcgaga cgctgctcaa gggcacgctc ttcccggtac    2940
gcctaccttc gatccgactt ctcccttgca tttctgacat tagcacaaca gaacttcggg    3000
caacgtcgga gaggtgatgt cccccatcgc gggtgagatg cgtctgcagt ccgacttcga    3060
gctcgcacaa gactctcgta ctgcttgcga gtggcagtcg ttcgtcagtg cgtgccctct    3120
ccttcccttt cgccccgccc ggattctctg accgtacacc agacaaccag gacaagatca    3180
agaccgcgtt tgctgccgcg ttcgccaaga tggccaccct cggaaatgac aggagccaga    3240
tggtcgactc ctccgaggtg ctgccagggg tctcgaccgc cactctcccg cccgcgcacc    3300
tccccgccgg caagacgctc gccgacgtcc agcaggctgt acgcacttca tattcactct    3360
gtgcgcgaga agttgagctg acgataccstg cttcagtgcg ccgacacccc cttcccgtct    3420
ctctctgccg accccggccc ggccaccact gtcccccctg tgtaagtgtt atacgataca    3480
```

-continued

```
attccctcag cgacggtgtg ctaacgtgat aaattcgtgc agcccgcctt cctaagttgc    3540
catctagtca gtcgagacgg tatatcgact gaggcgtcgt ctcatctgtc ggaagtagaa    3600
gttctgcgaa tgtatctatc tgttgattcg aatggggatc cgcttttgtg aac           3653
```

<210> SEQ ID NO 4
<211> LENGTH: 366
<212> TYPE: PRT
<213> ORGANISM: Bjerkandera adusta

<400> SEQUENCE: 4

```
Met Ala Phe Lys Gln Leu Leu Ala Thr Val Ser Leu Ala Phe Ser Leu
 1               5                  10                  15

Thr Ala Val Glu Ala Ala Leu Thr Arg Arg Val Ala Cys Pro Asp Gly
            20                  25                  30

Val Asn Thr Ala Thr Asn Ala Ala Cys Cys Ser Leu Phe Ala Ile Arg
        35                  40                  45

Asp Asp Leu Gln Gln Ser Leu Phe Asp Asn Gly Gly Cys Gly Glu Asp
    50                  55                  60

Val His Glu Ser Leu Arg Leu Thr Phe His Asp Ala Ile Gly Ile Ser
65                  70                  75                  80

Pro Ala Ile Ala Ala Thr Gly Lys Phe Gly Gly Gly Ala Asp Gly
                85                  90                  95

Ser Ile Ala Ile Phe Glu Asp Ile Glu Thr Asn Phe His Ala Asn Leu
            100                 105                 110

Gly Val Asp Glu Ile Ile Asn Glu Gln Arg Pro Ile Leu Ala Arg His
        115                 120                 125

Asn Ile Thr Thr Ala Asp Phe Ile Gln Phe Ala Gly Ala Val Gly Val
    130                 135                 140

Ser Asn Cys Pro Gly Ala Pro Gln Leu Glu Phe Leu Phe Gly Gly Arg
145                 150                 155                 160

Thr Asp Ala Thr Gln Pro Ala Pro Asp Leu Thr Val Pro Glu Pro Ser
                165                 170                 175

Asp Thr Val Asp Ser Ile Ile Ala Arg Phe Ala Asp Ala Gly Gly Phe
            180                 185                 190

Thr Pro Ala Glu Ile Val Ala Leu Leu Ala Ser His Thr Val Ala Ala
        195                 200                 205

Ala Asp His Val Asp Pro Thr Ile Pro Gly Thr Pro Phe Asp Ser Thr
    210                 215                 220

Ala Ser Thr Phe Asp Ser Gln Phe Val Glu Thr Leu Leu Lys Gly
225                 230                 235                 240

Thr Leu Phe Pro His Asn Arg Thr Ser Gly Asn Val Gly Glu Val Met
                245                 250                 255

Ser Pro Ile Ala Gly Glu Met Arg Leu Gln Ser Asp Phe Glu Leu Ala
            260                 265                 270

Gln Asp Ser Arg Thr Ala Cys Glu Trp Gln Ser Phe Val Asn Asn Gln
        275                 280                 285

Asp Lys Ile Lys Thr Ala Phe Ala Ala Phe Ala Lys Met Ala Thr
    290                 295                 300

Leu Gly Asn Asp Arg Ser Gln Met Val Asp Cys Ser Glu Val Leu Pro
305                 310                 315                 320

Arg Val Ser Thr Ala Thr Leu Pro Pro Ala His Leu Pro Ala Gly Lys
                325                 330                 335

Thr Leu Ala Asp Val Gln Gln Ala Cys Ala Asp Thr Pro Phe Pro Ser
            340                 345                 350
```

Leu Ser Ala Asp Pro Gly Pro Ala Thr Thr Val Pro Pro Val
         355                 360                 365

<210> SEQ ID NO 5
<211> LENGTH: 4810
<212> TYPE: DNA
<213> ORGANISM: Bjerkandera adusta

<400> SEQUENCE: 5

| | | | | |
|---|---|---|---|---|
| cgcatcttca | tccccggcac | gaagggcctg | cagcttgccc | gcgtaaattt | cgcgcgccat | 60 |
| acggtccaaa | gtatctataa | catccttcaa | ttcgtgtatg | gcccggcttg | gcgcgtgctc | 120 |
| cacgaggaat | cgctttaccc | gcgatgatgg | gatatacttc | acgagtggag | aaaagaaagc | 180 |
| aaagacagcg | cattttgcga | gggccggcct | ggaaagcgct | agatgtgagt | tccgagatcc | 240 |
| actctttctc | tggccgatgc | tcacactatg | tgcttgactg | cttccgcata | ctcgttgcga | 300 |
| gtgtcttcga | caaggctgtc | aaaggagtag | cccataccgc | cttgtccaat | aagctccaat | 360 |
| gcagcacggc | ccaatccatc | taagcatgtc | caattcgaca | ctttctgatc | ccttgacctg | 420 |
| ccgcgcgatg | ccatccttga | gctgagtcaa | gttgattaat | tatatgccgg | tacggggtac | 480 |
| cggcaagaca | cctacgcggt | ggacggtctc | gtagaacaca | ggcgttaggt | tcttcatatt | 540 |
| tcccagcgag | aaaacaggat | tgagcagctt | cctttggcgg | cggtggtgat | gacctagaac | 600 |
| ggtccgacgc | atggtcaagg | tgaacggccg | atgcagactc | gtaggacact | gcttaccatg | 660 |
| cgtggataac | agcccaggc | cgaagacaat | gtttcgatat | ctgaaggatg | gtgcacacgg | 720 |
| ttcagtgcac | ggtcggagat | ggagaagcgg | aattggataa | ctcacgcgag | tacgtagttt | 780 |
| ggttccggat | acatgtcctg | atccttgaga | acgatataat | gcagcgcctt | cgggtcaaac | 840 |
| acgtaaagcc | cccttcgctg | aaaaaacaaa | gggattcagc | ggaaagtcgc | acggtagaga | 900 |
| ggatcacgca | cgccgaacaa | cgaacggaac | ttgaccactg | caccatagtt | gtcgctgaga | 960 |
| tggtctatga | acgccatacc | gccttctcgc | tgaaagagct | gtttgaagtt | tcctgagagg | 1020 |
| agtcaaagtc | tagcggcgcc | gagattgtac | gactctcgac | cttacctgtg | aggaatgaag | 1080 |
| gggacggagg | cccaggtatc | ttgtctagag | gcgattccac | ggtcaacgca | cggaagacct | 1140 |
| tccatatcag | ccatgccaca | acaaaggaaa | tgcccgccga | tggtgcggag | agcgtcatgg | 1200 |
| tcgtagtaga | aagtgcgcag | acgtggggat | ggcgagtctg | tttcgccttg | atgtccgacc | 1260 |
| gtagccgtcg | ggtgagcgtt | agcgaagcag | cgtcatcact | gtcgcgtatt | ccttgttagt | 1320 |
| aacacaagat | ctccgcggtt | tcaatgtggc | tcttgctgta | ggggcccagg | gagggtgggg | 1380 |
| ggtgttcaac | gaccgcagta | gcttcggaaa | cccctcctcc | cacaccaagt | gagcttctga | 1440 |
| catgaattaa | tcgtcaagca | ctacccgcag | ctgtttgaag | tacaaaggta | ggtgataatc | 1500 |
| aggaaacctg | gagtgtgaga | gaccccatta | aagtgactga | ccgacggccg | cgcgatatcg | 1560 |
| tcttcaggct | gttgtttgat | tgttaaaaag | actatttcct | gcagcgaaac | tttatagaac | 1620 |
| ccatcgttgc | tgcggtcatg | atcgaagtta | acaggtgcct | ggtcaaaggt | caggcccatt | 1680 |
| tgtagcattt | gttggacata | gtgggcacca | accttggcgt | tgaagacaag | agaacgaatg | 1740 |
| acgattcggg | aattggatca | gcatgctgga | cgtctccgcc | agtattatct | acactccgca | 1800 |
| gggaagccgc | cggggccgaa | tgttgcggag | ccgagcggac | taggaacagg | cgcgcggaga | 1860 |
| ccgccggtac | actcgtattc | ttcctccgca | gcgagttgtt | tgaacaggac | tgtcgcttct | 1920 |
| gatttgtttc | tgtaccagat | acttctatcc | gattgcgcg | cgtcggatgt | gctcgctgac | 1980 |
| cttcatccag | ccctctgtgc | cctggtttta | caggttattt | ttgaagcccg | aacttccatc | 2040 |

-continued

```
tcctgcttct acggactgcc ccgtacaaat gtgaagagcg acatcgcgct ccgcaggcct    2100
ctgtgacctc caggaattct ctacagcggg accctgcagg tacgtgtgcg acaatcactg    2160
cggcaccaag tcggcttgcc aacgattgcc tttttctata gaccgagtgt cgggtcggtc    2220
ccgcgctggc gcacccagac ctcctccgga atgtagttcg tgctgtgcaa acatgcacca    2280
ctggaaactc cgcctcgcgt taggactagc gccaaatgcg gtcgcctctc gcgagtacct    2340
attgcactgc ttgcacaggg cttctctcgc gtatcaagcc actggcgaat acatcacaag    2400
cgggcccgtg agctgcgttg cagcaaatgc gcagtctgta gagtccagct ctcgaataca    2460
aacagactgc gcgtggctcg ggcaggccgg tcgcatcatg aaacgagggt cagatgccgg    2520
cagcgacgac cacggtccgc ggacgaggtt gggggggatga tgcccgactg gagaatggcg    2580
gtgctcctat tgggcccggg cgctgttggc ttggctggtc ggctccgggg tggtcgatct    2640
ccaccacgtt tatcgaagcc cgtcgcgctg gcggatcaca gatccaccac cataccactt    2700
ccagtataaa gagcgccggg tatgcaagcg aacacctcat cgtcccttcc cttctctcct    2760
ttcctctaat cccctccttc gttggtcgtc gacatggtgt tctacagact ctcctccctc    2820
cttgtgtctg ttgctgctat ccacgccgca gccggtacgc cacataatgg ctccccctc    2880 ccgatccacg ctgaccagct tgctaggtgc tctgacgcgc cgtgtcgcat gcccggatgg    2940
cgtgaacacc gcgaccaacg cggcgtgctg ccccttgtac gccgtccgcg atgacatgca    3000
ggccaacctg tatgatggtg gcgcgtgcaa cgccgaggtg catgagtccc tccgcctgtg    3060
agtacccagc ttgctttcgg tgttgcacaa agctcatcta gtgccagcac attccacgac    3120
gccattggta cgtcttgctt agatttcttc caacggtgtc ttacgatatt ctacaggcta    3180
ctccccagcc ctcgccgccg ccggctcatt cgcaggtgga ggagctgacg gctctatcct    3240
taccttcagc gatgttgaag cggccttctt tgccaacgcg ggtctcgacg agatgatcga    3300
gctccagaag ccatacatca ccaagtacaa catgactcct ggcgatgtgt acgtaccagg    3360
aacctctttg gcgatattat actgaagcgt ctctatagcc ttcaatttgc tggcgccgtc    3420
ggtctcagta actgcccagg tgctccgcaa ctggagttcc ttctcggtac gtcacgcaat    3480
aaatcagacc gcgaaagcca cgttctgatc atcgcccagg tcgtactgcc gctacggccg    3540
cgtcgcccac aggcctcatt cccgcaccct ttgacacggt cgatgcgatc attgcgcgct    3600
tcgccgacgt cgacttcagc gttgacgaga ttgtagcgct gttggcatcg taagcacgcc    3660 cccttttgctt ggcgagcatc atgattaacg acgtctcact tgcaggcact cggtcgccgc    3720
tgcaagccac atcgacacca ccgttcctga gtcgccgctc gactcgaccc ctggcgtctt    3780
cgacacccag ttcttcgtcg aaacctcgct caacggcacc atgtaccctg gtacctctgg    3840
aaacatcggc gaggccctgt cagcgattgc gggagagctt cgcctgctct cggaccatga    3900
gctcgcgcgt gactcgcgca ctgcctgcga gtggcagtcc tacgtcagta cgtaccctgt    3960
ccttcggttc cgttgacggt ttccatttat gctttacgtg tgcagacaac cagtccaaga    4020
tccagagcgc gttccgtgct gccatggcga ggatggccgt catcggccag gactcctcga    4080
ccatgattga ctgcaccgaa gtcatcccca ccgcatcgtc cttcacctcc gccgcgttta    4140
tccccgccgg tctcacctac gctgacatcg aacagtcgtg cgactccact cccttcccca    4200
ccctttctgt cgttgccggc gcggccacgt ccgtcgctgc cgttgcgtga gttgtttcgg    4260
ttcctctcaa attccacata gtactgacaa atatttaga aaatcataaa ctgcccacac    4320
cggcaacccc tggcttctat tctatctttt tgggttaata tggacttctt gaacacttgt    4380
```

-continued

```
ggttgaaatt ggattgaatt agtactgtcg ctacctgccc ggacctttgt aaacactgtc      4440
tgtctctacg agtaaatagc ccgctccaaa accgtctatc tatagaggta tccactgcca      4500
aatgtcatcg ctattatctg tctacatttt gctgcgcgac ataaaaaccc gatatggact      4560
tctcgtcgac attgtggcgc cgcagcaaag cggtctaacc gcaaatggca ggtatgtttt      4620
gaaatctcgg cctgctgttg tacctcaaaa tactcaagta cgttctcaca tgttcgcgcg      4680
atgaccgtac agcaactcca cggttgtggc gaagcagtcg aaaattaaat ggagcaggca      4740
ccactcactt ggcatctgcc atgtcacggt cctctggagt ctgagccaag acaaaactgg      4800
atcggggcat                                                             4810
```

<210> SEQ ID NO 6
<211> LENGTH: 362
<212> TYPE: PRT
<213> ORGANISM: Bjerkandera adusta

<400> SEQUENCE: 6

```
Met Val Phe Tyr Arg Leu Ser Ser Leu Leu Val Ser Val Ala Ala Ile
 1               5                  10                  15

His Ala Ala Ala Gly Ala Leu Thr Arg Arg Val Ala Cys Pro Asp Gly
             20                  25                  30

Val Asn Thr Ala Thr Asn Ala Ala Cys Cys Pro Leu Tyr Ala Val Arg
         35                  40                  45

Asp Asp Met Gln Ala Asn Leu Tyr Asp Gly Gly Ala Cys Asn Ala Glu
     50                  55                  60

Val His Glu Ser Leu Arg Leu Thr Phe His Asp Ala Ile Gly Tyr Ser
 65                  70                  75                  80

Pro Ala Leu Ala Ala Ala Gly Ser Phe Ala Gly Gly Gly Ala Asp Gly
                 85                  90                  95

Ser Ile Leu Thr Phe Ser Asp Val Glu Ala Ala Phe Phe Ala Asn Ala
            100                 105                 110

Gly Leu Asp Glu Met Ile Glu Leu Gln Lys Pro Tyr Ile Thr Lys Tyr
        115                 120                 125

Asn Met Thr Pro Gly Asp Val Val Gln Phe Ala Gly Ala Val Gly Leu
    130                 135                 140

Ser Asn Cys Pro Gly Ala Pro Gln Leu Glu Phe Leu Leu Gly Arg Thr
145                 150                 155                 160

Ala Ala Thr Ala Ala Ser Pro Thr Gly Leu Ile Pro Ala Pro Phe Asp
                165                 170                 175

Thr Val Asp Ala Ile Ile Ala Arg Phe Ala Asp Val Asp Phe Ser Val
            180                 185                 190

Asp Glu Ile Val Ala Leu Leu Ala Ser His Ser Val Ala Ala Ala Ser
        195                 200                 205

His Ile Asp Thr Thr Val Pro Glu Ser Pro Leu Asp Ser Thr Pro Gly
    210                 215                 220

Val Phe Asp Thr Gln Phe Phe Val Glu Thr Ser Leu Asn Gly Thr Met
225                 230                 235                 240

Tyr Pro Gly Thr Ser Gly Asn Ile Gly Glu Ala Leu Ser Ala Ile Ala
                245                 250                 255

Gly Glu Leu Arg Leu Leu Ser Asp His Glu Leu Ala Arg Asp Ser Arg
            260                 265                 270

Thr Ala Cys Glu Trp Gln Ser Tyr Val Asn Asn Gln Ser Lys Ile Gln
        275                 280                 285

Ser Ala Phe Arg Ala Ala Met Ala Arg Met Ala Val Ile Gly Gln Asp
```

```
                  290                 295                 300
Ser Ser Thr Met Ile Asp Cys Thr Glu Val Ile Pro Thr Ala Ser Ser
305                 310                 315                 320

Phe Thr Ser Ala Ala Phe Ile Pro Ala Gly Leu Thr Tyr Ala Asp Ile
                325                 330                 335

Glu Gln Ser Cys Asp Ser Thr Pro Phe Pro Thr Leu Ser Val Val Ala
                340                 345                 350

Gly Ala Ala Thr Ser Val Ala Val Ala
            355                 360

<210> SEQ ID NO 7
<211> LENGTH: 26
<212> TYPE: DNA
<213> ORGANISM: Artificial Sequence
<220> FEATURE:
<223> OTHER INFORMATION: Bjerkandera adusta
<221> NAME/KEY: misc_feature
<222> LOCATION: (0)...(0)
<223> OTHER INFORMATION: y= C or T
<221> NAME/KEY: misc_feature
<222> LOCATION: (0)...(0)
<223> OTHER INFORMATION: n= inosine

<400> SEQUENCE: 7
gtngcntgyc cngayggngt naayac                                        26

<210> SEQ ID NO 8
<211> LENGTH: 20
<212> TYPE: DNA
<213> ORGANISM: Artificial Sequence
<220> FEATURE:
<223> OTHER INFORMATION: Bjerkandera adusta
<221> NAME/KEY: misc_feature
<222> LOCATION: (0)...(0)
<223> OTHER INFORMATION: n= inosine
<221> NAME/KEY: misc_feature
<222> LOCATION: (0)...(0)
<223> OTHER INFORMATION: r= A or G

<400> SEQUENCE: 8
tgnggngcnc cnggrcartt                                               20

<210> SEQ ID NO 9
<211> LENGTH: 26
<212> TYPE: DNA
<213> ORGANISM: Artificial Sequence
<220> FEATURE:
<223> OTHER INFORMATION: Bjerkandera adusta
<221> NAME/KEY: misc_feature
<222> LOCATION: (0)...(0)
<223> OTHER INFORMATION: n= inosine
<221> NAME/KEY: misc_feature
<222> LOCATION: (0)...(0)
<223> OTHER INFORMATION: y= C or T

<400> SEQUENCE: 9
gtngcntgyc cngayggngt naayac                                        26

<210> SEQ ID NO 10
<211> LENGTH: 19
<212> TYPE: DNA
<213> ORGANISM: Artificial Sequence
<220> FEATURE:
<223> OTHER INFORMATION: Bjerkandera adusta
<221> NAME/KEY: misc_feature
<222> LOCATION: (0)...(0)
<223> OTHER INFORMATION: n= inosine
<221> NAME/KEY: misc_feature
```

-continued

```
<222> LOCATION: (0)...(0)
<223> OTHER INFORMATION: y= C or T
<221> NAME/KEY: misc_feature
<222> LOCATION: (0)...(0)
<223> OTHER INFORMATION: r= A or G

<400> SEQUENCE: 10
tgccaytcrc angcngtnc                                              19
```

POLYPEPTIDES HAVING PEROXIDASE ACTIVITY AND NUCLEIC ACIDS ENCODING SAME

BACKGROUND OF THE INVENTION

1. Field of the Invention

The present invention relates to isolated polypeptides having peroxidase activity and isolated nucleic acid sequences encoding the polypeptides. The invention also relates to nucleic acid constructs, vectors, and host cells comprising the nucleic acid sequences as well as methods for producing and using the polypeptides.

2. Description of the Related Art

Lignin is an aromatic polymer occurring in the woody tissue of higher plants. Due to its hydrophobicity and complex random structure lacking regular hydrolysable bonds, lignin is poorly degraded by most organisms. The best degraders of lignin are white rot fungi that produce extracellular peroxidases and laccases, which are involved in the initial attack of lignin.

Manganese-dependent peroxidase is a frequently encountered peroxidase produced by white rot fungi. The peroxidase has a catalytic cycle involving a 2-electron oxidation of the heme by hydrogen peroxide and subsequent oxidation of compound I via compound II in two 1-electron steps to the native enzyme. The best reducing substrate for compounds I and II is Mn(II), a metal naturally present in wood. The Mn(III) formed oxidizes other substrates.

Organic acids such as oxalate, glyoxylate and lactate are known to have an important role in the mechanism of manganese-dependent peroxidase and lignin degradation. Mn(III) is stripped from the enzyme by organic acids, and the produced Mn(III)-organic acid complex acts as a diffusible mediator in the oxidation of lignin by manganese-dependent peroxidase. Mn(III) can also oxidize organic acids, yielding radicals. The organic acids may also be supplied from the degradation of lignin and by microorganisms.

Field and Mester, 1998, *Journal of Biochemistry* 273: 15412–15417, disclose a manganese peroxidase-lignin peroxidase hybrid produced by Bjerkandera sp. strain BOS55, which is able to oxidize various substrates in the absence of manganese.

It is an object of the present invention to provide improved polypeptides having peroxidase activity and nucleic acid encoding the polypeptides.

SUMMARY OF THE INVENTION

The present invention relates to isolated polypeptides having peroxidase activity selected from the group consisting of:

(a) a polypeptide having an amino acid sequence which has at least 75% identity with amino acids 22 to 370 of SEQ ID NO: 2, amino acids 22 to 365 of SEQ ID NO: 4, or amino acids 19 to 362 of SEQ ID NO: 6;

(b) a polypeptide encoded by a nucleic acid sequence which hybridizes under high stringency conditions with (i) nucleotides 775 to 2302 of SEQ ID NO: 1, nucleotides 2011 to 3462 of SEQ ID NO: 3, or nucleotides 2851 to 4257 of SEQ ID NO: 5, (ii) the cDNA sequence contained in nucleotides 775 to 2302 of SEQ ID NO: 1, nucleotides 2011 to 3462 of SEQ ID NO: 3, or nucleotides 2851 to 4257 of SEQ ID NO: 5, (iii) a subsequence of (i) or (ii) of at least 100 nucleotides, or (iv) a complementary strand of (i), (ii), or (iii);

(c) a variant of the polypeptide having an amino acid sequence of SEQ ID NO: 2, SEQ ID NO: 4, or SEQ ID NO: 6 comprising a substitution, deletion, and/or insertion of one or more amino acids;

(d) an allelic variant of (a) or (b); and (e) a fragment of (a), (b), or (d) that has peroxidase activity.

The present invention also relates to isolated nucleic acid sequences encoding the polypeptides and to nucleic acid constructs, vectors, and host cells comprising the nucleic acid sequences as well as methods for producing and using the polypeptides.

BRIEF DESCRIPTION OF THE FIGURES

FIGS. 1A, B, and C show the genomic DNA sequence and the deduced amino acid sequence of a *Bjerkandera adusta* ATCC 90940 peroxidase (SEQ ID NOs: 1 and 2, respectively).

FIGS. 2A, B, C, and D show the genomic DNA sequence and the deduced amino acid sequence of a *Bjerkandera adusta* ATCC 90940 peroxidase (SEQ ID NOs: 3 and 4, respectively).

FIGS. 3A, B, C, D, and E show the genomic DNA sequence and the deduced amino acid sequence of a *Bjerkandera adusta* ATCC 90940 peroxidase (SEQ ID NOs: 5 and 6, respectively).

DETAILED DESCRIPTION OF THE INVENTION

Polypeptides Having Peroxidase Activity

The term "peroxidase activity" is defined herein as an oxidation-reduction activity that catalyzes the oxidation of a suitable reducing substrate ($H^+$ donor) by hydrogen peroxide through the formation of a heme intermediate. When the reducing substrate is Mn(II) ion, the peroxidase activity is then specified as manganese peroxidase activity.

For purposes of the present invention, peroxidase activity is measured according to the procedure described by Mester and Field, 1998, *Journal of Biological Chemistry* 273: 15412–15417, where the oxidation of Mn(II) is monitored by the formation of Mn(III)-malonate complex at 270 nm or by the secondary oxidation of phenol red with Mn(II) at 600 nm and pH 4.5. Peroxidase activity may also be measured by monitoring the oxidation of 2,6-dimethoxyphenol to coerulignone, ABTS to ABTS+, and veratryl alcohol to veratraldehyde at 469, 420, and 310 nm, respectively, and pH 7.0. One unit of peroxidase activity is defined as 1.0 µmole of hydrogen peroxidase consumed per minute at 25° C., pH 4.5 or pH 7.

In a first embodiment, the present invention relates to isolated polypeptides having an amino acid sequence which has a degree of identity to amino acids 22 to 370 of SEQ ID NO: 2, amino acids 22 to 365 of SEQ ID NO: 4, or amino acids 19 to 362 of SEQ ID NO: 6 (i.e., the mature polypeptide) of at least about 75%, preferably at least about 80%, more preferably at least about 85%, even more preferably at least about 90%, most preferably at least about 95%, and even most preferably at least about 97%, which have peroxidase activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from amino acids 22 to 370 of SEQ ID NO: 2, amino acids 22 to 365 of SEQ ID NO: 4, or amino acids 19 to 362 of SEQ ID NO: 6. For purposes of the present invention, the degree of identity between two amino acid sequences is determined by the Clustal method (Higgins, 1989, *CABIOS* 5: 151–153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5.

Preferably, the polypeptides of the present invention comprise the amino acid sequence of SEQ ID NO: 2 or an allelic variant thereof; or a fragment thereof that has peroxidase activity. In a more preferred embodiment, the polypeptide of the present invention comprises the amino acid sequence of SEQ ID NO: 2. In another preferred embodiment, the polypeptide of the present invention comprises amino acids 22 to 370 of SEQ ID NO: 2, or an allelic variant thereof; or a fragment thereof that has peroxidase activity. In another preferred embodiment, the polypeptide of the present invention comprises amino acids 22 to 370 of SEQ ID NO: 2. In another preferred embodiment, the polypeptide of the present invention consists of the amino acid sequence of SEQ ID NO: 2 or an allelic variant thereof; or a fragment thereof that has peroxidase activity. In another preferred embodiment, the polypeptide of the present invention consists of the amino acid sequence of SEQ ID NO: 2. In another preferred embodiment, the polypeptide consists of amino acids 22 to 370 of SEQ ID NO: 2 or an allelic variant thereof; or a fragment thereof that has peroxidase activity. In another preferred embodiment, the polypeptide consists of amino acids 22 to 370 of SEQ ID NO: 2.

Preferably, the polypeptides of the present invention comprise the amino acid sequence of SEQ ID NO: 4 or an allelic variant thereof; or a fragment thereof that has peroxidase activity. In a more preferred embodiment, the polypeptide of the present invention comprises the amino acid sequence of SEQ ID NO: 4. In another preferred embodiment, the polypeptide of the present invention comprises amino acids 22 to 365 of SEQ ID NO: 4, or an allelic variant thereof, or a fragment thereof that has peroxidase activity. In another preferred embodiment, the polypeptide of the present invention comprises amino acids 22 to 365 of SEQ ID NO: 4. In another preferred embodiment, the polypeptide of the present invention consists of the amino acid sequence of SEQ ID NO: 4 or an allelic variant thereof; or a fragment thereof that has peroxidase activity. In another preferred embodiment, the polypeptide of the present invention consists of the amino acid sequence of SEQ ID NO: 4. In another preferred embodiment, the polypeptide consists of amino acids 22 to 365 of SEQ ID NO: 4 or an allelic variant thereof; or a fragment thereof that has peroxidase activity. In another preferred embodiment, the polypeptide consists of amino acids 22 to 365 of SEQ ID NO: 4.

Preferably, the polypeptides of the present invention comprise the amino acid sequence of SEQ ID NO: 6 or an allelic variant thereof; or a fragment thereof that has peroxidase activity. In a more preferred embodiment, the polypeptide of the present invention comprises the amino acid sequence of SEQ ID NO: 6. In another preferred embodiment, the polypeptide of the present invention comprises amino acids 19 to 362 of SEQ ID NO: 6, or an allelic variant thereof; or a fragment thereof that has peroxidase activity. In another preferred embodiment, the polypeptide of the present invention comprises amino acids 19 to 362 of SEQ ID NO: 6. In another preferred embodiment, the polypeptide of the present invention consists of the amino acid sequence of SEQ ID NO: 6 or an allelic variant thereof; or a fragment thereof that has peroxidase activity. In another preferred embodiment, the polypeptide of the present invention consists of the amino acid sequence of SEQ ID NO: 6. In another preferred embodiment, the polypeptide consists of amino acids 19 to 363 of SEQ ID NO: 6 or an allelic variant thereof; or a fragment thereof that has peroxidase activity. In another preferred embodiment, the polypeptide consists of amino acids 19 to 363 of SEQ ID NO: 6.

A fragment of SEQ ID NO: 2 is a polypeptide having one or more amino acids deleted from the amino and/or carboxyl terminus of this amino acid sequence. Preferably, a fragment contains at least 295 amino acid residues, more preferably at least 315 amino acid residues, and most preferably at least 335 amino acid residues.

A fragment of SEQ ID NO: 4 is a polypeptide having one or more amino acids deleted from the amino and/or carboxyl terminus of this amino acid sequence. Preferably, a fragment contains at least 285 amino acid residues, more preferably at least 305 amino acid residues, and most preferably at least 325 amino acid residues.

A fragment of SEQ ID NO: 6 is a polypeptide having one or more amino acids deleted from the amino and/or carboxyl terminus of this amino acid sequence. Preferably, a fragment contains at least 285 amino acid residues, more preferably at least 305 amino acid residues, and most preferably at least 325 amino acid residues.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

In a second embodiment, the present invention relates to isolated polypeptides having peroxidase activity which are encoded by nucleic acid sequences which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with (i) nucleotides 775 to 2302 of SEQ ID NO: 1, nucleotides 2011 to 3462 of SEQ ID NO: 3, or nucleotides 2851 to 4257 of SEQ ID NO: 5, (ii) the cDNA sequence contained in nucleotides 775 to 2302 of SEQ ID NO: 1, nucleotides 2011 to 3462 of SEQ ID NO: 3, or nucleotides 2851 to 4257 of SEQ ID NO: 5, (iii) a subsequence of (i) or (ii), or (iv) a complementary strand of (i), (ii), or (iii) (J. Sambrook, E. F. Fritsch, and T. Maniatus, 1989, *Molecular Cloning, A Laboratory Manual,* 2d edition, Cold Spring Harbor, N.Y.). The subsequence of SEQ ID NO: 1 may be at least 100 nucleotides or preferably at least 200 nucleotides. Moreover, the subsequence may encode a polypeptide fragment which has peroxidase activity. The polypeptides may also be allelic variants or fragments of the polypeptides that have peroxidase activity.

The nucleic acid sequence of SEQ ID NO: 1, SEQ ID NO: 3, or SEQ ID NO: 5, or a subsequence thereof; as well as the amino acid sequence of SEQ ID NO: 2, SEQ ID NO: 4, or SEQ ID NO: 6, or a fragment thereof, may be used to design a nucleic acid probe to identify and clone DNA encoding polypeptides having peroxidase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

Thus, a genomic DNA or cDNA library prepared from such other organisms may be screened for DNA which hybridizes with the probes described above and which encodes a polypeptide having peroxidase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 1, SEQ ID NO: 3, or SEQ ID NO: 5, or a subsequence of SEQ ID NO: 1, SEQ ID NO: 3, or SEQ ID NO: 5, the carrier material is used in a Southern blot. For purposes of the present invention, hybridization indicates that the nucleic acid sequence hybridizes to a labeled nucleic acid probe corresponding to the nucleic acid sequence shown in SEQ ID NO: 1, SEQ ID NO: 3, or SEQ ID NO: 5, as well as a complementary strand or a subsequence of these sequences, under very low to very high stringency conditions. Molecules to which the nucleic acid probe hybridizes under these conditions are detected using X-ray film.

In a preferred embodiment, the nucleic acid probe is a nucleic acid sequence which encodes the polypeptide of SEQ ID NO: 2, or a subsequence thereof. In another preferred embodiment, the nucleic acid probe is SEQ ID NO: 1. In another preferred embodiment, the nucleic acid probe is the mature polypeptide coding region of SEQ ID NO: 1. In another preferred embodiment, the nucleic acid probe is the nucleic acid sequence contained in plasmid pBM37-7 which is contained in *Escherichia coli* NRRL B-30280, wherein the nucleic acid sequence encodes a polypeptide having peroxidase activity. In another preferred embodiment, the nucleic acid probe is the mature polypeptide coding region contained in plasmid pBM37-7 which is contained in *Escherichia coli* NRRL B-30280.

In a preferred embodiment, the nucleic acid probe is a nucleic acid sequence which encodes the polypeptide of SEQ ID NO: 4, or a subsequence thereof. In another preferred embodiment, the nucleic acid probe is SEQ ID NO: 3. In another preferred embodiment, the nucleic acid probe is the mature polypeptide coding region of SEQ ID NO: 3. In another preferred embodiment, the nucleic acid probe is the nucleic acid sequence contained in plasmid pBM38-1 which is contained in *Escherichia coli* NRRL B-30281, wherein the nucleic acid sequence encodes a polypeptide having peroxidase activity. In another preferred embodiment, the nucleic acid probe is the mature polypeptide coding region contained in plasmid pBM38-1 which is contained in *Escherichia coli* NRRL B-30281.

In a preferred embodiment, the nucleic acid probe is a nucleic acid sequence which encodes the polypeptide of SEQ ID NO: 6, or a subsequence thereof. In another preferred embodiment, the nucleic acid probe is SEQ ID NO: 5. In another preferred embodiment, the nucleic acid probe is the mature polypeptide coding region of SEQ ID NO: 5. In another preferred embodiment, the nucleic acid probe is the nucleic acid sequence contained in plasmid pBM39-1 which is contained in *Escherichia coli* NRRL B-30282, wherein the nucleic acid sequence encodes a polypeptide having peroxidase activity. In another preferred embodiment, the nucleic acid probe is the mature polypeptide coding region contained in plasmid pBM39-1 which is contained in *Escherichia coli* NRRL B-30282.

For long probes of at least 100 nucleotides in length, very low to very high stringency conditions are defined as prehybridization and hybridization at 42° C. in 5×SSPE, 0.3% SDS, 200 $\mu$g/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third embodiment, the present invention relates to variants of the polypeptide having an amino acid sequence of SEQ ID NO: 2, SEQ ID NO: 4, or SEQ ID NO: 6 comprising a substitution, deletion, and/or insertion of one or more amino acids.

The amino acid sequences of the variant polypeptides may differ from the amino acid sequence of SEQ ID NO: 2, SEQ ID NO: 4, or SEQ ID NO: 6, or the mature polypeptides thereof, by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a fourth embodiment, the present invention relates to isolated polypeptides having immunochemical identity or partial immunochemical identity to the polypeptide having the amino acid sequence of SEQ ID NO: 2 or the mature polypeptide thereof. The immunochemical properties are determined by immunological cross-reaction identity tests by the well-known Ouchterlony double immunodiffusion procedure. Specifically, an antiserum containing polyclonal antibodies which are immunoreactive or bind to epitopes of the polypeptide having the amino acid sequence of SEQ ID NO: 2 or the mature polypeptide thereof are prepared by immunizing rabbits (or other rodents) according to the procedure described by Harboe and Ingild, In N. H. Axelsen, J. Krøll, and B. Weeks, editors, *A Manual of Quantitative Immunoelectrophoresis*, Blackwell Scientific Publications, 1973, Chapter 23, or Johnstone and Thorpe, *Immunochemistry in Practice*, Blackwell Scientific Publications, 1982 (more specifically pages 27–31). A polypeptide having immunochemical identity is a polypeptide which reacts with the antiserum in an identical fashion such as total fusion of precipitates, identical precipitate morphology, and/or identical electrophoretic mobility using a specific immunochemical technique. A further explanation of immunochemical identity is described by Axelsen, Bock, and Krøll, In N. H. Axelsen, J. Krøll, and B. Weeks, editors, *A Manual of Quantitative Immunoelectrophoresis*, Blackwell Scientific Publications, 1973, Chapter 10. A polypeptide having partial immunochemical identity is a polypeptide which reacts with the antiserum in a partially identical fashion such as partial fusion of precipitates, partially identical precipitate morphology, and/or partially identical electrophoretic mobility using a specific immunochemical technique. A further explanation of partial immunochemical identity is described by Bock and Axelsen, In N. H. Axelsen, J. Krøll, and B. Weeks, editors, *A Manual of Quantitative Immunoelectrophoresis*, Blackwell Scientific Publications, 1973, Chapter 11.

The antibody may also be a monoclonal antibody. Monoclonal antibodies may be prepared and used, e.g., according to the methods of E. Harlow and D. Lane, editors, 1988, *Antibodies, A Laboratory Manual*, Cold Spring Harbor Press, Cold Spring Harbor, N.Y.

The polypeptides of the present invention have at least 20%, preferably at least 40%, more preferably at least 60%, even more preferably at least 80%, even more preferably at least 90%, and most preferably at least 100% of the peroxidase activity of the mature polypeptide of SEQ ID NO: 2, SEQ ID NO: 4, or SEQ ID NO: 6.

A polypeptide of the present invention may be obtained from microorganisms of any genus. For purposes of the present invention, the term "obtained from" as used herein in connection with a given source shall mean that the polypeptide encoded by the nucleic acid sequence is produced by the source or by a cell in which the nucleic acid sequence from the source has been inserted. In a preferred embodiment, the polypeptide is secreted extracellularly.

A polypeptide of the present invention may be a fungal polypeptide, and more preferably a yeast polypeptide such as a Candida, Kluyveromyces, Pichia, Saccharomyces, Schizosaccharomyces, or Yarrowia polypeptide; or more preferably a filamentous fungal polypeptide such as an Acremonium, Aspergillus, Aureobasidium, Bjerkandera, Cryptococcus, Filibasidium, Fusarium, Humicola, Magnaporthe, Mucor, Myceliophthora, Neocallimastix, Neurospora, Paecilomyces, Penicillium, Piromyces, Polyporus, Schizophyllum, Talaromyces, Thermoascus, Thielavia, Tolypocladium, or Trichoderma polypeptide.

In a preferred embodiment, the polypeptide is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* polypeptide.

In another preferred embodiment, the polypeptide is an *Aspergillus aculeatus, Aspergillus awamori, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei*, or *Trichoderma viride* polypeptide.

In another preferred embodiment, the polypeptide is a *Bjerkandera adusta, Bjerkandera fumosa, Polyporus adustus, Polyporus crispus, Polyporus halesiae, Polyporus fumosus*, or *Polyporus halesiae* polypeptide.

In a more preferred embodiment, the polypeptide is a *Bjerkandera adusta* polypeptide, and most preferably a *Bjerkandera adusta* ATCC 90940 polypeptide, e.g., the polypeptide with the amino acid sequence of SEQ ID NO: 2, SEQ ID NO: 4, or SEQ ID NO: 6.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents. For example, taxonomic equivalents of Bjerkandera are defined by Farr et al., 1989, *Fungi on Plants and Plant Products in the United States*, APS Press, St. Paul, Minn. For instance, synonyms of *Bjerkandera adusta* are *Polyporus adustus, Polyporus crispus*, and *Polyporus halesiae*.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

As defined herein, an "isolated" polypeptide is a polypeptide which is essentially free of other non-peroxidase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

Polypeptides encoded by nucleic acid sequences of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Nucleic Acid Sequences

The present invention also relates to isolated nucleic acid sequences which encode a polypeptide of the present invention. In a preferred embodiment, the nucleic acid sequence is set forth in SEQ ID NO: 1. In another more preferred embodiment, the nucleic acid sequence is the sequence contained in plasmid pBM37-7 that is contained in *Escherichia coli* NRRL B-30280. In another preferred embodiment, the nucleic acid sequence is the mature polypeptide coding region of SEQ ID NO: 1. In another more preferred embodiment, the nucleic acid sequence is the mature polypeptide coding region contained in plasmid pBM37-7 that is contained in *Escherichia coli* NRRL B-30280. The present invention also encompasses nucleic acid sequences which encode a polypeptide having the amino acid sequence of SEQ ID NO: 2 or the mature polypeptide thereof, which differ from SEQ ID NO: 1 by virtue of the degeneracy of the genetic code. The present invention also relates to subsequences of SEQ ID NO: 1 which encode fragments of SEQ ID NO: 2 that have peroxidase activity.

In another preferred embodiment, the nucleic acid sequence is set forth in SEQ ID NO: 3. In another more preferred embodiment, the nucleic acid sequence is the sequence contained in plasmid pBM38-1 that is contained in *Escherichia coli* NRRL B-30281. In another preferred embodiment, the nucleic acid sequence is the mature polypeptide coding region of SEQ ID NO: 3. In another more preferred embodiment, the nucleic acid sequence is the mature polypeptide coding region contained in plasmid pBM38-1 that is contained in *Escherichia coli* NRRL B-30281. The present invention also encompasses nucleic acid sequences which encode a polypeptide having the amino acid sequence of SEQ ID NO: 4 or the mature polypeptide thereof, which differ from SEQ ID NO: 3 by virtue of the degeneracy of the genetic code. The present invention also relates to subsequences of SEQ ID NO: 3 which encode fragments of SEQ ID NO: 4 that have peroxidase activity.

In another preferred embodiment, the nucleic acid sequence is set forth in SEQ ID NO: 5. In another more preferred embodiment, the nucleic acid sequence is the sequence contained in plasmid pBM39-1 that is contained in *Escherichia coli* NRRL B-30282. In another preferred embodiment, the nucleic acid sequence is the mature polypeptide coding region of SEQ ID NO: 5. In another more preferred embodiment, the nucleic acid sequence is the mature polypeptide coding region contained in plasmid pBM39-1 that is contained in *Escherichia coli* NRRL B-30282. The present invention also encompasses nucleic acid sequences which encode a polypeptide having the amino acid sequence of SEQ ID NO: 6 or the mature polypeptide thereof, which differ from SEQ ID NO: 5 by virtue of the degeneracy of the genetic code. The present invention also relates to subsequences of SEQ ID NO: 5 which encode fragments of SEQ ID NO: 6 that have peroxidase activity.

A subsequence of SEQ ID NO: 1, SEQ ID NO: 3, or SEQ ID NO: 5 is a nucleic acid sequence encompassed by SEQ ID NO: 1, SEQ ID NO: 3, or SEQ ID NO: 5, respectively, except that one or more nucleotides from the 5' and/or 3' end have been deleted. Preferably, a subsequence of SEQ ID NO: 1 contains at least 885 nucleotides, more preferably at least 945 nucleotides, and most preferably at least 1005 nucleotides. Preferably, a subsequence of SEQ ID NO: 3 contains at least 855 nucleotides, more preferably at least 915 nucleotides, and most preferably at least 975 nucleotides. Preferably, a subsequence of SEQ ID NO: 5 contains at least 855 nucleotides, more preferably at least 915 nucleotides, and most preferably at least 975 nucleotides.

The present invention also relates to mutant nucleic acid sequences comprising at least one mutation in the mature polypeptide coding sequence of SEQ ID NO: 1, SEQ ID NO: 3, or SEQ ID NO: 5, in which the mutant nucleic acid sequence encodes a polypeptide which consists of amino acids 22 to 370 of SEQ ID NO: 2, amino acids 22 to 365 of SEQ ID NO: 4, or amino acids 19 to 362 of SEQ ID NO: 6, respectively.

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application,* Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of Bjerkandera, or another or related organism and thus, for example, may be an allelic or species variant of the polypeptide encoding region of the nucleic acid sequence.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The present invention also relates to nucleic acid sequences which have a degree of homology to the mature polypeptide coding sequence of SEQ ID NO: 1 (i.e., nucleotides 775 to 2302), SEQ ID NO: 3 (i.e., nucleotides 2011 to 3462), SEQ ID NO: 5 (i.e., nucleotides 2851 to 4257) of at least about 75%, preferably about 80%, preferably about 85%, more preferably about 90%, even more preferably about 95%, and most preferably about 97% homology, which encode an active polypeptide. For purposes of the present invention, the degree of homology between two nucleic acid sequences is determined by the Wilbur-Lipman method (Wilbur and Lipman, 1983, *Proceedings of the National Academy of Science USA* 80: 726–730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=3, gap penalty=3, and windows=20.

Modification of a nucleic acid sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant sequence may be constructed on the basis of the nucleic acid sequence presented as the polypeptide encoding part of SEQ ID NO: 1, SEQ ID NO: 3, or SEQ ID NO: 5, e.g., a subsequence thereof, and/or by introduction of nucleotide substitutions which do not give rise to another amino acid sequence of the polypeptide encoded by the nucleic acid sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081–1085). In the latter technique, mutations are introduced at every positively charged residue in the molecule, and the resultant mutant molecules are tested for peroxidase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306–312; Smith et al., 1992, *Journal of Molecular Biology* 224: 899–904; Wlodaver et al., 1992, *FEBS Letters* 309: 59–64).

The present invention also relates to isolated nucleic acid sequences encoding a polypeptide of the present invention, which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with the nucleic acid sequence of SEQ ID NO: 1, SEQ ID NO: 3, or SEQ ID NO: 5; or its complementary strand; or allelic variants and subsequences thereof (Sambrook et al., 1989, supra), as defined herein.

The present invention also relates to isolated nucleic acid sequences produced by (a) hybridizing a DNA under very low, low, medium, medium-high, high, or very high stringency conditions with (i) nucleotides 775 to 2302 of SEQ ID NO: 1, nucleotides 2011 to 3462 of SEQ ID NO: 3, or nucleotides 2851 to 4257 of SEQ ID NO: 5, (ii) the cDNA sequence contained in nucleotides 775 to 2302 of SEQ ID NO: 1, nucleotides 2011 to 3462 of SEQ ID NO: 3, or nucleotides 2851 to 4257 of SEQ ID NO: 5, (iii) a subsequence of (i) or (ii), or (iv) a complementary strand of (i), (ii), or (iii); and (b) isolating the nucleic acid sequence. The subsequence is preferably a sequence of at least 100 nucleotides such as a sequence which encodes a polypeptide fragment which has peroxidase activity.

Methods for Producing Mutant Nucleic Acid Sequences

The present invention further relates to methods for producing a mutant nucleic acid sequence, comprising introducing at least one mutation into the mature polypeptide coding sequence of SEQ ID NO: 1, SEQ ID NO: 3, or SEQ ID NO: 5; or a subsequence thereof; wherein the mutant nucleic acid sequence encodes a polypeptide which consists of amino acids 22 to 370 of SEQ ID NO: 2, amino acids 22 to 365 of SEQ ID NO: 4, or amino acids 19 to 362 of SEQ ID NO: 6; or a fragment thereof which has peroxidase activity.

The introduction of a mutation into the nucleic acid sequence to exchange one nucleotide for another nucleotide may be accomplished by site-directed mutagenesis using any of the methods known in the art. Particularly useful is the procedure which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used.

Nucleic Acid Constructs

The present invention also relates to nucleic acid constructs comprising a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. The term nucleic acid construct is synonymous with the term expression cassette when the nucleic acid construct contains all the control sequences required for expression of a coding sequence of the present invention. The term "coding sequence" is defined herein as a nucleic acid sequence which directly specifies the amino acid sequence of its protein product. The boundaries of a genomic coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The term "control sequences" is defined herein to include all components which are necessary or advantageous for the expression of a polypeptide of the present invention. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the expression of a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8:

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983–5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

In a preferred embodiment, the signal peptide coding region is nucleotides 733 to 774 of SEQ ID NO: 1 which encode amino acids 1 to 21 of SEQ ID NO: 2; nucleotides 1949 to 2011 of SEQ ID NO: 3 which encode amino acids 1 to 21 of SEQ ID NO: 4; or nucleotides 2797 to 2850 of SEQ ID NO: 5 which encode amino acids I to 18 of SEQ ID NO: 6.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

The present invention also relates to nucleic acid constructs for altering the expression of an endogenous gene encoding a polypeptide of the present invention. The constructs may contain the minimal number of components necessary for altering expression of the endogenous gene. In one embodiment, the nucleic acid constructs preferably contain (a) a targeting sequence, (b) a regulatory sequence, (c) an exon, and (d) a splice-donor site. Upon introduction of the nucleic acid construct into a cell, the construct inserts by homologous recombination into the cellular genome at the endogenous gene site. The targeting sequence directs the integration of elements (a)–(d) into the endogenous gene such that elements (b)–(d) are operably linked to the endogenous gene. In another embodiment, the nucleic acid constructs contain (a) a targeting sequence, (b) a regulatory sequence, (c) an exon, (d) a splice-donor site, (e) an intron, and (f) a splice-acceptor site, wherein the targeting sequence directs the integration of elements (a)–(f) such that elements (b)–(f) are operably linked to the endogenous gene. However, the constructs may contain additional components such as a selectable marker.

In both embodiments, the introduction of these components results in production of a new transcription unit in which expression of the endogenous gene is altered. In essence, the new transcription unit is a fusion product of the sequences introduced by the targeting constructs and the endogenous gene. In one embodiment in which the endogenous gene is altered, the gene is activated. In this embodiment, homologous recombination is used to replace, disrupt, or disable the regulatory region normally associated with the endogenous gene of a parent cell through the insertion of a regulatory sequence which causes the gene to be expressed at higher levels than evident in the corresponding parent cell. The activated gene can be further amplified by the inclusion of an amplifiable selectable marker gene in the construct using methods well known in the art (see, for example, U.S. Pat. No. 5,641,670). In another embodiment in which the endogenous gene is altered, expression of the gene is reduced.

The targeting sequence can be within the endogenous gene, immediately adjacent to the gene, within an upstream gene, or upstream of and at a distance from the endogenous gene. One or more targeting sequences can be used. For example, a circular plasmid or DNA fragment preferably employs a single targeting sequence, while a linear plasmid or DNA fragment preferably employs two targeting sequences.

The regulatory sequence of the construct can be comprised of one or more promoters, enhancers, scaffold-attachment regions or matrix attachment sites, negative regulatory elements, transcription binding sites, or combinations of these sequences.

The constructs further contain one or more exons of the endogenous gene. An exon is defined as a DNA sequence which is copied into RNA and is present in a mature mRNA molecule such that the exon sequence is in-frame with the coding region of the endogenous gene. The exons can, optionally, contain DNA which encodes one or more amino acids and/or partially encodes an amino acid. Alternatively, the exon contains DNA which corresponds to a 5' non-encoding region. Where the exogenous exon or exons encode one or more amino acids and/or a portion of an amino acid, the nucleic acid construct is designed such that, upon transcription and splicing, the reading frame is in-frame with the coding region of the endogenous gene so that the appropriate reading frame of the portion of the mRNA derived from the second exon is unchanged.

The splice-donor site of the constructs directs the splicing of one exon to another exon. Typically, the first exon lies 5' of the second exon, and the splice-donor site overlapping and flanking the first exon on its 3' side recognizes a splice-acceptor site flanking the second exon on the 5' side of the second exon. A splice-acceptor site, like a splice-donor site, is a sequence which directs the splicing of one exon to another exon. Acting in conjunction with a splice-donor site, the splicing apparatus uses a splice-acceptor site to effect the removal of an intron.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an Aspergillus cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the nucleic acid sequence encoding the polypeptide or any other element of the vector for integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location (s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75:1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a eukaryote, such as a mammalian, insect, plant, or fungal cell.

In a preferred embodiment, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred embodiment, the yeast host cell is a Candida, Hansenula, Kluyveromyces, Pichia, Saccharomyces, Schizosaccharomyces, or Yarrowia cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, or Trichoderma.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81: 1470–1474. Suitable methods for transforming Fusarium species are described by Malardier et al., 1989, *Gene* 78: 147–156, and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182–187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention comprising (a) cultivating a strain, which in its wild-type form is capable of producing the polypeptide, to produce the polypeptide; and (b) recovering the polypeptide. Preferably, the strain is of the genus Bjerkandera, and more preferably *Bjerkandera adusta*.

The present invention also relates to methods for producing a polypeptide of the present invention comprising (a) cultivating a host cell under conditions conducive for production of the polypeptide; and (b) recovering the polypeptide.

The present invention also relates to methods for producing a polypeptide of the present invention comprising (a) cultivating a host cell under conditions conducive for production of the polypeptide, wherein the host cell comprises a mutant nucleic acid sequence having at least one mutation in the mature polypeptide coding region of SEQ ID NO: 1, SEQ ID NO: 3, or SEQ ID NO: 5 wherein the mutant nucleic acid sequence encodes a polypeptide which consists of amino acids 22 to 370 of SEQ ID NO: 2, amino acids 22 to 365 of SEQ ID NO: 4, or amino acids 19 to 362 of SEQ ID NO: 6, respectively, and (b) recovering the polypeptide.

The present invention further relates to methods for producing a polypeptide of the present invention comprising (a) cultivating a homologously recombinant cell, having incorporated therein a new transcription unit comprising a regulatory sequence, an exon, and/or a splice donor site operably linked to a second exon of an endogenous nucleic acid sequence encoding the polypeptide, under conditions conducive for production of the polypeptide; and (b) recovering the polypeptide. The methods are based on the use of gene activation technology, for example, as described in U.S. Pat. No. 5,641,670.

In the production methods of the present invention, the cells are cultivated in a nutrient medium suitable for production of the polypeptide using methods known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Plants

The present invention also relates to a transgenic plant, plant part, or plant cell which has been transformed with a nucleic acid sequence encoding a polypeptide having peroxidase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as festuca, lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers. Also specific plant tissues, such as chloroplast, apoplast, mitochondria, vacuole, peroxisomes, and cytoplasm are considered to be a plant part. Furthermore, any plant cell, whatever the tissue origin, is considered to be a plant part.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV promoter may be used (Franck et al., 1980, *Cell* 21: 285–294). Organ-specific promoters may be, for example, a promoter from storage sink tissues such as seeds, potato tubers, and fruits (Edwards & Coruzzi, 1990, *Ann. Rev. Genet.* 24: 275–303), or from metabolic sink tissues such as meristems (Ito et al., 1994, *Plant Mol. Biol.* 24: 863–878), a seed specific promoter such as the glutelin, prolamin, globulin, or albumin promoter from rice (Wu et al., 1998, *Plant and Cell Physiology* 39: 885–889), a *Vicia faba* promoter from the legumin B4 and the unknown seed protein gene from *Vicia faba* (Conrad et al., 1998, *Journal of Plant Physiology* 152: 708–711), a promoter from a seed oil body protein (Chen et al., 1998, Plant and Cell Physiology 39: 935–941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991–1000, the chlorella virus adenine methyltransferase gene promoter (Mitra and Higgins, 1994, *Plant Molecular Biology* 26: 85–93), or the aldP gene promoter from rice (Kagaya et al., 1995, *Molecular and General Genetics* 248: 668–674), or a wound inducible promoter such as the potato pin2 promoter (Xu et al., 1993, *Plant Molecular Biology* 22: 573–588).

A promoter enhancer element may also be used to achieve higher expression of the enzyme in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including Agrobacterium-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al, 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15–38). However it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275–281; Shimamoto, 1994, *Current Opinion Biotechnology* 5: 158–162; Vasil et al., 1992, *Bio/Technology* 10: 667–674). An alternative method for transformation of monocots is based on protoplast transformation as described by Omirulleh et al., 1993, *Plant Molecular Biology* 21: 415–428.

Following transformation, the transformants having incorporated therein the expression construct are selected and regenerated into whole plants according to methods well-known in the art.

The present invention also relates to methods for producing a polypeptide of the present invention comprising (a) cultivating a transgenic plant or a plant cell comprising a nucleic acid sequence encoding a polypeptide having peroxidase activity of the present invention under conditions conducive for production of the polypeptide; and (b) recovering the polypeptide.

Removal or Reduction of Peroxidase Activity

The present invention also relates to methods for producing a mutant cell of a parent cell, which comprises disrupting or deleting a nucleic acid sequence encoding the polypeptide or a control sequence thereof, which results in the mutant cell producing less of the polypeptide than the parent cell when cultivated under the same conditions.

The construction of strains which have reduced peroxidase activity may be conveniently accomplished by modification or inactivation of a nucleic acid sequence necessary for expression of the polypeptide having peroxidase activity in the cell. The nucleic acid sequence to be modified or inactivated may be, for example, a nucleic acid sequence encoding the polypeptide or a part thereof essential for exhibiting peroxidase activity, or the nucleic acid sequence may have a regulatory function required for the expression of the polypeptide from the coding sequence of the nucleic acid sequence. An example of such a regulatory or control sequence may be a promoter sequence or a functional part thereof, i.e., a part which is sufficient for affecting expression of the polypeptide. Other control sequences for possible modification are described above.

Modification or inactivation of the nucleic acid sequence may be performed by subjecting the cell to mutagenesis and selecting or screening for cells in which the peroxidase producing capability has been reduced. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the cell to be mutagenized in the presence of the mutagenizing agent of choice under suitable conditions, and selecting for cells exhibiting reduced peroxidase activity or production.

Modification or inactivation of production of a polypeptide of the present invention may be accomplished by introduction, substitution, or removal of one or more nucleotides in the nucleic acid sequence encoding the polypeptide or a regulatory element required for the transcription or translation thereof. For example, nucleotides may be inserted or removed so as to result in the introduction of a stop codon, the removal of the start codon, or a change of the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleic acid sequence to be modified, it is preferred that the modification be performed in vitro as exemplified below.

An example of a convenient way to eliminate or reduce production by a host cell of choice is by gene replacement or gene interruption. In the gene interruption method, a nucleic acid sequence corresponding to the endogenous gene or gene fragment of interest is mutagenized in vitro to produce a defective nucleic acid sequence which is then transformed into the host cell to produce a defective gene. By homologous recombination, the defective nucleic acid sequence replaces the endogenous gene or gene fragment. It may be desirable that the defective gene or gene fragment also encodes a marker which may be used for selection of transformants in which the gene encoding the polypeptide has been modified or destroyed.

Alternatively, modification or inactivation of the nucleic acid sequence may be performed by established anti-sense techniques using a nucleotide sequence complementary to the polypeptide encoding sequence. More specifically, production of the polypeptide by a cell may be reduced or eliminated by introducing a nucleotide sequence complementary to the nucleic acid sequence encoding the polypeptide which may be transcribed in the cell and is capable of hybridizing to the polypeptide mRNA produced in the cell. Under conditions allowing the complementary anti-sense nucleotide sequence to hybridize to the polypeptide mRNA, the amount of polypeptide translated is thus reduced or eliminated.

It is preferred that the cell to be modified in accordance with the methods of the present invention is of microbial origin, for example, a fungal strain which is suitable for the production of desired protein products, either homologous or heterologous to the cell.

The present invention further relates to a mutant cell of a parent cell which comprises a disruption or deletion of a nucleic acid sequence encoding the polypeptide or a control sequence thereof, which results in the mutant cell producing less of the polypeptide than the parent cell.

The polypeptide-deficient mutant cells so created are particularly useful as host cells for the expression of homologous and/or heterologous polypeptides. Therefore, the present invention further relates to methods for producing a homologous or heterologous polypeptide comprising (a) cultivating the mutant cell under conditions conducive for production of the polypeptide; and (b) recovering the polypeptide. The term "heterologous polypeptides" is defined herein as polypeptides which are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method for producing a protein product essentially free of peroxidase activity by fermentation of a cell which produces both a polypeptide of the present invention as well as the protein product of interest by adding an effective amount of an agent capable of inhibiting peroxidase activity to the fermentation broth before, during, or after the fermentation has been completed, recovering the product of interest from the fermentation broth, and optionally subjecting the recovered product to further purification.

In a further aspect, the present invention relates to a method for producing a protein product essentially free of peroxidase activity by cultivating the cell under conditions permitting the expression of the product, subjecting the resultant culture broth to a combined pH and temperature treatment so as to reduce the peroxidase activity substantially, and recovering the product from the culture broth. Alternatively, the combined pH and temperature treatment may be performed on an enzyme preparation recovered from the culture broth. The combined pH and temperature treatment may optionally be used in combination with a treatment with a peroxidase inhibitor.

In accordance with this aspect of the invention, it is possible to remove at least 60%, preferably at least 75%, more preferably at least 85%, still more preferably at least 95%, and most preferably at least 99% of the peroxidase activity. Complete removal of peroxidase activity may be obtained by use of this method.

The combined pH and temperature treatment is preferably carried out at a pH in the range of 6.5–7 and a temperature in the range of 25–40° C. for a sufficient period of time to attain the desired effect, where typically, 30 to 60 minutes is sufficient.

The methods used for cultivation and purification of the product of interest may be performed by methods known in the art.

The methods of the present invention for producing an essentially peroxidase-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulytic enzyme, oxidoreductase, or plant cell-wall degrading enzyme. Examples of such enzymes include an aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The peroxidase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from peroxidase activity which is produced by a method of the present invention.

Compositions

In a still further aspect, the present invention relates to compositions comprising a polypeptide of the present invention. Preferably, the compositions are enriched in a polypeptide of the present invention. In the present context, the term "enriched" indicates that the peroxidase activity of the composition has been increased, e.g., with an enrichment factor of 1.1.

The composition may comprise a polypeptide of the invention as the major enzymatic component, e.g., a monocomponent composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be producible by means of a microorganism belonging to the genus Aspergillus, preferably *Aspergillus aculeatus, Aspergillus awamori, Aspergillus niger,* or *Aspergillus oryzae,* or Trichoderma, Humicola, preferably *Humicola insolens,* or Fusarium, preferably *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides,* or *Fusarium venenatum.*

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to methods for using the polypeptides having peroxidase activity.

The peroxidases can be used in number of different industrial processes. These processes include polymerization of lignin, both Kraft and lignosulfates, in order to produce a lignin with a higher molecular weight. A neutral/alkaline peroxidase is a particular advantage in that Kraft lignin is more soluble at higher pHs. Such methods are described in, for example, Jin et al., 1991, *Holzforschung* 45: 467–468; U.S. Pat. No. 4,432,921; EP 0 275 544; PCT/DK93/00217, 1992. Peroxidase is also useful in the copolymerization of lignin with low molecular weight compounds, such as is described by Milstein et al, 1994, *Appl. Microbiol. Biotechnology* 40: 760–767.

The peroxidases of the present invention can also be used for in-situ depolymerization of lignin in Kraft pulp, thereby producing a pulp with lower lignin content. This use of peroxidase is an improvement over the current use of chlorine for depolymerization of lignin, which leads to the production of chlorinated aromatic compounds, which are an environmentally undesirable by-product of paper mills. Such uses are described in, for example, *Current Opinion in Biotechnology* 3: 261–266, 1992; *Journal of Biotechnology* 25: 333–339, 1992; Hiroi et al., *Svensk Papperstidning* 5:162–166, 1976.

Oxidation of dyes or dye precursors and other chromophoric compounds leads to decolorization of the compounds. Peroxidase can be used for this purpose, which can be particularly advantageous in a situation in which a dye transfer between fabrics is undesirable, e.g., in the textile industry and in the detergent industry. Methods for dye transfer inhibition and dye oxidation can be found in WO 92/01406; WO 92/18683; WO 92/18687; WO 91/05839; EP 0495836; Calvo, 1991, *Mededelingen van de Faculteit Landbouw-wetenschappen/Rijiksuniversitet Gent.* 56: 1565–1567; Tsujino et al., 1991, *J. Soc. Chem.* 42: 273–282.

Use of peroxidase in oxidation of dye precursors for hair dyeing is disclosed in U.S. Pat. No. 3,251,742, the contents of which are incorporated herein by reference.

The present peroxidases can also be used for the polymerization or oxidation of phenolic compounds present in liquids. An example of such utility is the treatment of juices, such as apple juice, so that the peroxidase will accelerate a precipitation of the phenolic compounds present in the juice, thereby producing a more stable juice. Such applications have been described in Stutz, 1993, *Fruit Processing* 7/93, 248–252; Maier et al., 1990, *Dt. Lebensmittel-rindschau* 86: 137–142; Dietrich et al., 1990, *Fluss. Obst* 57: 67–73.

Peroxidases of the present invention are also useful in soil detoxification (Nannipieri et al., 1991, *J. Environ. Qual.* 20: 510–517; Dec and Bollag, 1990, *Arch. Environ. Contam. Toxicol.* 19: 543–550).

Signal Peptide

The present invention also relates to nucleic acid constructs comprising a gene encoding a protein operably linked to a nucleic acid sequence consisting of nucleotides 733 to 774 of SEQ ID NO: 1, nucleotides 1949 to 2011 of SEQ ID NO: 3, or nucleotides 2797 to 2850 of SEQ ID NO: 5 encoding a signal peptide consisting of amino acids 1–21 of SEQ ID NO: 2, amino acids 1 to 21 of SEQ ID NO: 4, or amino acids 1 to 18 of SEQ ID NO: 6, respectively, wherein the gene is foreign to the nucleic acid sequence.

The present invention also relates to recombinant expression vectors and recombinant host cells comprising such nucleic acid constructs.

The present invention also relates to methods for producing a protein comprising (a) cultivating such a recombinant host cell under conditions suitable for production of the protein; and (b) recovering the protein.

The nucleic acid sequence may be operably linked to foreign genes with other control sequences. Such other control sequences are described supra. As noted earlier, where both signal peptide and propeptide regions are present at the amino terminus of a protein, the propeptide region is positioned next to the amino terminus of a protein and the signal peptide region is positioned next to the amino terminus of the propeptide region.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides which comprise a combination of partial or complete polypeptide sequences obtained from at least two different proteins wherein one or more may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred embodiment, the protein is an oxidoreductase, transferase, hydrolase, lyase, isomerase, or ligase. In an even more preferred embodiment, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples which should not be construed as limiting the scope of the invention.

EXAMPLES

Chemicals used as buffers and substrates were commercial products of at least reagent grade.

Fungal Strain

*Bjerkandera adusta* strain ATCC 90940 was used as the source of genomic DNA.

Bacterial Strains and Cloning Vectors

Plasmid pCR2.1-TOPO (Invitrogen, San Diego, Calif.) was used for the cloning of the PCR amplified peroxidase gene fragments. *Escherichia coli* TOP10 (Invitrogen, San Diego, Calif.) was used as the host for cloning and maintenance of PCR products.

Plasmid pBluescript II KS(−) (Stratagene, La Jolla, Calif.) was used for the cloning of the partial HindIII digested genomic DNA from *Bjerkandera adusta* ATCC 90940. *E. coli* SoloPack Gold supercompetent cells (Stratagene, LaJolla, Calif.) and XL10-Gold Kan ultracompetent cells (Stratagene, LaJolla, Calif.) were used to construct the partial *Bjerkandera adusta* genomic library.

Media

*Bjerkandera adusta* strain ATCC 90940 was grown in YEG media composed of 1% yeast extract and 2% peptone.

Example 1

Genomic DNA Isolation

Genomic DNA was prepared from *Bjerkandera adusta* strain ATCC 90940 using a Qiagen Maxi Column (Qiagen, Valencia, Calif.) according to the manufactuer's protocol. The mycelia were collected through Miracloth (Calbiochem, La Jolla, Calif.) and rinsed twice with TE buffer (10 mM Tris-1 mM EDTA). The mycelia were frozen in liquid nitrogen and ground to a fine powder in an electric coffee grinder that was prechilled with dry ice. Approximately two grams of powder were transferred to a disposable 50 ml conical tube followed by 20 ml of lysis buffer (100 mM EDTA, 10 mM Tris, 1% Triton X-100, 500 mM guanidine-HCl, 200 mM NaCl pH 5.0). The mixture was incubated at 37° C. for 30 minutes after addition of 20 μg of DNase-free RNase per ml. Proteinase K was added at 0.8 mg/ml and incubated at 50° C. for 2 hours. A Qiagen Maxi column (Qiagen, Valencia, Calif.) was equilibrated with 10 ml of QBT buffer (Qiagen, Valencia, Calif.). The cleared lysate was transferred to the column to bind genomic DNA. The column was washed twice with 30 ml of QC buffer. DNA was eluted with 15 ml of QF buffer (Qiagen, Valencia, Calif.). A 10.5 ml volume of room temperature filter-sterilized isopropanol was added and mixed gently. The DNA was pelleted by centrifugation at 1500×g for 20 minutes. The pellet was washed with ice-cold 70% ethanol and then air-dried. The dried pellet was resuspended in TE buffer.

Example 2

PCR Amplification

Degenerate primers were designed based on the reported N-terminal amino acid sequence of a reported hybrid manganese/lignin peroxidase hybrid enzyme (Field and Mester, 1998, supra) and to conserved regions ("NCPGAPQ" and "RTACEWQ") found in fungal lignin and manganese peroxidases from various wood-degrading fungi. These primers were used to PCR amplify a peroxidase from *Bjerkandera adusta*.

Set1:
Primer 990355: 5'-GTIGCITGYCCIGAYGGIGTIAAYAC-3' (SEQ ID NO: 7)
Primer 990356: 5'-TGIGGIGCICCIGGRCARTT-3' (SEQ ID NO: 8)
Set2:
Primer 990355: 5'-GTIGCITGYCCIGAYGGIGTIAAYAC-3' (SEQ ID NO: 9)
Primer 990357: 5'-TGCCAYTCRCAIGCIGTIC-3' (SEQ ID NO: 10)

PCR reactions (50 μl) were composed of 1.16 μg of *Bjerkandera adusta* genomic DNA as the template, 50 pmoles of primer set I or 2, and 1X HotStarTaq DNA polymerase Master Mix (Qiagen, Valencia, Calif.). The reactions were performed in an Ericomp Twin Block System Easy Cycler programmed as follows: Cycle 1 at 95° C. for 15 minutes; cycles 2–31 each at 95° C. for 30 seconds, 60° C. for 30 seconds, and 72° C. for 2 minutes; and cycle 32 at 72° C. for 10 minutes.

A 10 μl volume of each PCR reaction was electrophoresed for 1 hour at 100 volts on a 1% agarose gel using TAE buffer (40 mM Tris base, 20 mM sodium acetate, 1 mM disodium EDTA pH 7.2). The results revealed the presence of a PCR product of ~540 bp from primer set 1 and a PCR product of ~1050 bp from primer set 2.

The PCR product from primer set 1 (~540 bp) and the PCR product (~1050 bp) from primer set 2 were cloned into plasmid pCR2.1-TOPO and transformed into Invitrogen TOP10 cells according to the manufacturer's instructions.

Analysis of the TOPO clones was performed by DNA sequencing using a Perkin-Elmer Applied Biosystems Model 377 Sequencer XL (Perkin Elmer/Applied Biosystems Inc., Foster City, Calif.) with dye-terminator chemistry (Giesecke et al., 1992, *Journal of Virology Methods* 38: 47–60) and M13-forward and M13-reverse sequencing primers.

Sequence analysis suggested three independent clones, which were designated pBM37 (~540 bp insert), pBM38 (~540 bp insert), and pBM39 (~1050 bp insert).

Example 3
Southern Blot Analysis

Genomic DNA was analyzed by Southern Hybridization (Maniatis et al., 1982, Molecular Cloning, a Laboratory Manual, Cold Spring Harbor Press, Cold Spring Harbor, N.Y.). Approximately 1 μg of *Bjerkandera adusta* genomic DNA, prepared as described in Example 1, was digested separately with EcoRI, BamHI, HindIII, and SalI (Boehringer Mannheim, Indianapolis, Ind.) and fractionated by size on a 0.7% agarose gel using TAE buffer. The gel was photographed under short wavelength UV light and soaked twice for 15 minutes in 0.2 N HCl, followed by a brief rinse in double distilled water. DNA was transferred to a Hybond N+ hybridization membrane (Amersham Life Science, Arlington Heights, Ill.) by capillary blotting with 0.4 M NaOH using the Turbo Blot Method (Schleicher and Schuell, Keene, N.H.). The membrane was UV crosslinked (UV Stratalinker 2400, Stratagene, La Jolla, Calif.) and incubated for 2 hours in the following hybridization buffer at 65° C. with gentle agitation: 6xSSPE, 7% SDS.

pBM37, pBM38, and pBM39 were digested with EcoRI and electrophoresed on a 1% agarose gel using TAE buffer. Gene specific fragments from pBM37 (~540 bp), pBM38 (~540 bp), and pBM39 (~1040 bp) were gel purified using a Qiagen Gel Extraction Kit (Qiagen, Valencia, Calif.) followed by radiolabeling using random priming (Prime it II, Stratagene, La Jolla, Calif.). The radiolabeled fragment probes were added to the hybridization buffer at an activity of approximately $1 \times 10^6$ cpm per ml of buffer. The mixture was incubated with the membrane overnight at 65° C. in a shaking water bath. Following incubation, the membrane was washed twice for 15 minutes in 2xSSC with 0.1% SDS at 65° C., and once in 2xSSC for 15 minutes at room temperature. The membrane was wrapped in plastic wrap and exposed to X-ray film for 24 hours at −80° C. with intensifying screens (Kodak, Rochester, N.Y.).

All three fragments hybridized to DNA digested with HindIII. The pBM37 fragment hybridized to a 8.0 kb band, the pBM39 fragment to a 4.7 kb band, and the pBM38 fragment to a 3.9 kb band.

Example 4
*Bjerkandera adusta* Partial Genomic Library Construction and Screening of the Library for Peroxidase Genomic Clones A partial genomic library was constructed by partially digesting *Bjerkandera adusta* ATCC 90940 genomic DNA with HindIII. Thirty units of HindIII were used to digest 5.2 μg of *Bjerkandera adusta* genomic DNA using conditions recommended by the manufacturer. The reaction was carried out at 37° C., and samples were taken at 3 minute intervals from 17 to 30 minutes. The reactions were placed on ice and stopped by addition of 10xDNA loading dye (25% glycerol, 10 mM Tris pH 7.0, 10 mM EDTA, 0.025% bromophenol blue, 0.025% xylene cyanol). These digests were size fractionated on a 0.7% agarose gel using TAE buffer, and the region of the gel containing DNA ranging in size from 3 to 9 kb was excised. The excised DNA was gel purified using a Qiagen Gel Extraction kit (Qiagen, Valencia, Calif.) according to manufacturer's suggestions.

The size selected DNA was ligated into pBluescript II KS(−) previously digested with HindIII, and transformed into Solopack Gold Supercompetent cells and XL10-Gold Kan Ultracompetent cells.

The genomic library was screened to obtain genomic clones of peroxidase genes. The library was plated to obtain approximately 1000 colonies per 150-mm petri plate. The colonies were lifted to Hybond-N+ hybridization filters (Amersham Life Science, Arlington Heights, Ill.) using standard protocols (Samsbrook et al., 1989, supra). The filters were crosslinked with UV (UV Stratalinker 2400, Stratagene, La Jolla, Calif.) and incubated for 2 hours in 6xSSPE, 7% SDS at 65° C. with gentle agitation. The radiolabeled probes from pBM37, pBM38, and pBM39, as described in Example 3, were added to the hybridization buffer at an activity of approximately $1 \times 10^6$ cpm per ml of buffer. The mixture was incubated with the filters overnight at 65° C. in a shaking water bath. Following incubation, the filters were washed twice for fifteen minutes each time in 2xSSC with 0.1% SDS at 65° C., and once in 2xSSC for fifteen minutes at room temperature. The filters were wrapped in plastic wrap and exposed to X-ray film for 24 hours at −80° C. with intensifying screens.

Several positive colonies were identified and purified to homogeneity using standard protocols (Sambrook et al., 1989, supra). The three new clones were designated pBM37-7, pBM38-1 and pBM39-1, respectively.

Example 5
Analysis of Genomic Clones

DNA sequencing was performed with an Applied Biosystems Model 377 Sequencer XL using dye-terminator chemistry. Complete nucleotide sequences were generated using a transposon insertion strategy using a Primer Island Transposition Kit (Perkin Elmer/Applied Biosystems Inc., Foster City, Calif.).

The first clone (pBM37-7) was sequenced to a redundancy of 6.4. The nucleotide sequence and deduced amino acid sequence are shown in FIG. 1. The first 25 amino acids were identical to the N-terminal amino acid sequence of a hybrid manganese/lignin peroxidase from Bjerkandera adusta (Field and Mester, 1998, supra). The insert contained an open reading frame of 1110 bp encoding a protein of 370 amino acids. Using the SignalP program (Nielsen et al., 1997, Protein Engineering 10: 1–6), a signal peptide of 21 amino acid residues was predicted indicating the mature peroxidase contains 349 amino acids. There is one potential N-linked glycosylation site. Within the promoter region of clone pBM37-7, putative TATAAA and CAAT motifs can be found at positions −72 and −353, respectively.

The positions of introns and exons within the pBM37-7 peroxidase gene were assigned based on alignments of the deduced amino acid sequence to the other filamentous fungal peroxidase gene products. On the basis of this comparison, the Bjerkandera adusta ATCC 90940 pBM37-7 peroxidase gene is comprised of 10 exons (77, 138, 57, 135, 68, 54, 79, 126, 310, and 69 bp) which are interrupted by 9 small introns (49, 52, 53, 59, 56, 54, 53, 54, and 54 bp).

The pBM37-7 peroxidase gene has been deposited with the Agricultural Research Service Patent Culture Collection, Northern Regional Research Center, as E. coli NRRL B-30280.

The second clone (pBM38-1) was sequenced to a redundancy of 6.2. The nucleotide sequence and deduced amino acid sequence are shown in FIG. 2. The insert contained an open reading frame of 1095 bp encoding a protein of 365 amino acids. Using the SignalP program, a signal peptide of 21 residues was predicted indicating the mature peroxidase contains 344 amino acids. There are two potential N-linked glycosylation sites (Asn-X-Ser/Thr). Within the promoter region of clone pBM38-1, putative TATAAA and CAAT motifs can be found at positions −73 and −112, respectively.

The positions of introns and exons within the pBM38-1 peroxidase gene were assigned based on alignments of the deduced amino acid sequence to other filamentous fungal peroxidase gene products. On the basis of this comparison, the Bjerkandera adusta ATCC 90940 pBM38-1 peroxidase gene is comprised of 10 exons (60, 151, 57, 135, 68, 133, 124, 124, 176, and 69 bp) which are interrupted by 9 small introns (53, 54, 53, 50, 51, 55, 47, 55, and 58 bp).

The pBM38-1 peroxidase gene has been deposited with the Agricultural Research Service Patent Culture Collection, Northern Regional Research Center, as E. coli NRRL B-30281.

The third clone (pBM39-1) was sequenced to a redundancy of 6.0. The nucleotide sequence and deduced amino acid sequence are shown in FIG. 3. The insert contained an open reading frame of 1086 bp encoding a protein of 362 amino acids. Using the SignalP program, a signal peptide of 18 residues was predicted indicating the mature predicted peroxidase contains 344 amino acids. There are three potential N-linked glycosylation sites (Asn-X-Ser/Thr). The promoter region for this gene contains a TATAAA motif at position−89, but does not contain a CAAT motif.

The positions of introns and exons within the pBM39-1 peroxidase gene were assigned based on alignments of the deduced amino acid sequence to other filamentous fungal peroxidase gene products. On the basis of this comparison, the Bjerkandera adusta ATCC 90940 peroxidase gene is comprised of 8 exons (61, 151, 24, 172, 68, 130, 242, and 245 bp) which are interrupted by 7 small introns (52, 50, 45, 50, 53, 56, and 58 bp).

The pBM39-1 peroxidase gene has been deposited with the Agricultural Research Service Patent Culture Collection, Northern Regional Research Center, as E. coli NRRL B-30282.

A comparative alignment showed that deduced amino acid sequences of the pBM37-7 peroxidase gene shares 63.6% identity with a lignin peroxidase from Phanerochaete chrysosporium (Swissprot P11542).

A comparative alignment showed that the deduced amino acid sequences of the pBM38-1 and pBM39-1 peroxidases share 62.4% and 55.7% identity, respectively, with a lignin peroxidase from Trametes versicolor (Swissprot P20013).

Deposit of Biological Material

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
| --- | --- | --- |
| E. coli pBM37-7 | NRRL B-30280 | April 24, 2000 |
| E. coli pBM38-1 | NRRL B-30281 | April 24, 2000 |
| E. coli pBM39-1 | NRRL B-30282 | April 24, 2000 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. An isolated polypeptide having peroxidase activity, selected from the group consisting of:
   (a) a polypeptide having an amino acid sequence which has at least 75% identity with amino acids 22 to 370 of SEQ ID NO:2 or amino acids 19 to 362 of SEQ ID NO:6, or at least 85% identity with amino acids 22 to 365 of SEQ ID NO:4;
   (b) a polypeptide which is encoded by a nucleic acid sequence which hybridizes under high stringency conditions with (i) nucleotides 772 to 2302 of SEQ ID NO:1, nucleotides 2008 to 3462 of SEQ ID NO:3, or nucleotides 2848 to 4247 of SEQ ID NO:5, (ii) the cDNA sequence contained in nucleotides 772 to 2302 of SEQ ID NO:1, nucleotides 2008 to 3462 of SEQ ID NO:3, or nucleotides 2848 to 4247 of SEQ ID NO:5, or (iii) a complementary strand of (i) or (ii);
   (c) a fragment of (a), or (b), that has peroxidase activity.

2. The polypeptide of claim 1, having an amino acid sequence which has at least 75% identity with amino acids 22 to 370 of SEQ ID NO:2 or amino acids 19 to 362 of SEQ ID NO:6.

3. The polypeptide of claim 2, having an amino acid sequence which has at least 80% identity with amino acids 22 to 370 of SEQ ID NO:2 or amino acids 19 to 362 of SEQ ID NO:6.

4. The polypeptide of claim 3, having an amino acid sequence which has at least 85% identity with amino acids 22 to 370 of SEQ ID NO:2 or amino acids 19 to 362 of SEQ ID NO:6.

5. The polypeptide of claim 4, having an amino acid sequence which has at least 90% identity with amino acids 22 to 370 of SEQ ID NO:2 or amino acids 19 to 362 of SEQ ID NO:6.

6. The polypeptide of claim 5, having an amino acid sequence which has at least 95% identity with amino acids 22 to 370 of SEQ ID NO:2 or amino acids 19 to 362 of SEQ ID NO:6.

7. The polypeptide of claim 1, having an amino acid sequence which has at least 85% identity with amino acids 22 to 365 of SEQ ID NO:4.

8. The polypeptide of claim 7, having an amino acid sequence which has at least 90% identity with amino acids 22 to 365 of SEQ ID NO:4.

9. The polypeptide of claim 8, having an amino acid sequence which has at least 95% identity with amino acids 22 to 370 of SEQ ID NO:2 or amino acids 19 to 362 of SEQ ID NO:4.

10. The polypeptide of claim 1, comprising the amino acid sequence of SEQ ID NO:2, SEQ ID NO:4, or SEQ ID NO:6.

11. The polypeptide of claim 1, consisting of the amino acid sequence of SEQ ID NO:2, SEQ ID NO:4, or SEQ ID NO:6, or a fragment thereof having peroxidase activity.

12. The polypeptide of claim 11, consisting of the amino acid sequence of SEQ ID NO:2, SEQ ID NO:4, or SEQ ID NO:6.

13. The polypeptide of claim 11, which consists of amino acids 22 to 370 of SEQ ID NO:2, amino acids 22 to 365 of SEQ ID NO:4, or amino acids 19 to 362 of SEQ ID NO:6.

14. The polypeptide of claim 1, which is encoded by a nucleic acid sequence which hybridizes under high stringency conditions with (i) nucleotides 772 to 2302 of SEQ ID NO:1, nucleotides 2008 to 3462 of SEQ ID NO:3, or nucleotides 2848 to 4247 of SEQ ID NO:5, (ii) the cDNA sequence contained in nucleotides 772 to 2302 of SEQ ID NO:1, nucleotides 2008 to 3462 of SEQ ID NO:3, or nucleotides 2848 to 4247 of SEQ ID NO:5, or (iii) a complementary strand of (i) or (ii).

15. The polypeptide of claim 1, which is encoded by the nucleic acid sequence contained in plasmid pBM37-7 which is contained in *E. coli* NRRL B-30280, plasmid pBM38-1 which is contained in *E. coli* NRRL B-30281, or plasmid pBM39-1 which is contained in *E. coli* NRRL B-30282.

* * * * *